(12) United States Patent
Qi et al.

(10) Patent No.: US 8,575,143 B2
(45) Date of Patent: Nov. 5, 2013

(54) 3-ARYL-SUBSTITUTED QUINAZOLONES, AND USES THEREOF

(75) Inventors: Longwu Qi, West Lafayette, IN (US); Raj Gopal Venkat, Salt Lake City, UT (US); Michael Pierce, Salt Lake City, UT (US); Paul B. Robbins, Park City, UT (US); Sudhir R. Sahasrabudhe, Sandy, UT (US); Robert Selliah, Midvale, UT (US)

(73) Assignee: Prolexys Pharmaceuticals, Inc., Salt Lake City, UT (US)

( * ) Notice: Subject to any disclaimer, the term of this patent is extended or adjusted under 35 U.S.C. 154(b) by 836 days.

(21) Appl. No.: 12/086,900

(22) PCT Filed: Dec. 22, 2006

(86) PCT No.: PCT/US2006/049172
§ 371 (c)(1),
(2), (4) Date: Oct. 21, 2010

(87) PCT Pub. No.: WO2007/076087
PCT Pub. Date: Jul. 5, 2007

(65) Prior Publication Data
US 2011/0092489 A1  Apr. 21, 2011

Related U.S. Application Data

(60) Provisional application No. 60/753,801, filed on Dec. 22, 2005, provisional application No. 60/833,855, filed on Jul. 27, 2006.

(51) Int. Cl.
*A01N 55/02* (2006.01)
*C07D 239/70* (2006.01)
*C07D 223/00* (2006.01)

(52) U.S. Cl.
USPC ............................ 514/186; 544/253; 540/484

(58) Field of Classification Search
None
See application file for complete search history.

(56) References Cited

U.S. PATENT DOCUMENTS

2007/0161644 A1 * 7/2007 Stockwell ................ 514/252.17
2009/0214465 A1 * 8/2009 Becklin et al. ............... 424/85.2

FOREIGN PATENT DOCUMENTS

WO       WO 03106435 A1 * 12/2003
WO       WO 2006081337 A2 * 8/2006

OTHER PUBLICATIONS

Tani J et al.; "Studies on Biologically Active Halogenated Compounds II"; Nov. 1979; Chemical and Pharmaceutical Bulletin; vol. 27 pp. 2675-2687.*
Ager, I. R.; Harrison, D. R.; Kennewell, P. D.; Taylor, J. B., Synthesis and central nervous system activity of quinazolones related to 2-methyl-3-(o-tolyl)-4(3H)-quinazolone, 1977, JOurnal of Medicinal Chemistry, 20 (3), 379-86.*
World Health Organization, Guidelines on packaging for pharmaceutical products, 2002, WHO Technical Report Series, No. 902. 128-30.*

* cited by examiner

*Primary Examiner* — James O Wilson
*Assistant Examiner* — Oluwafemi Masha
(74) *Attorney, Agent, or Firm* — McAndrews, Held & Malloy, Ltd.

(57) ABSTRACT

Compounds represented by Structural Formula (I):

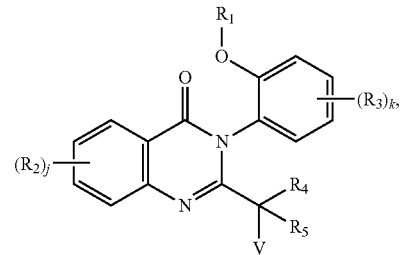

are useful, for example, in the effective killing or reducing the rate of proliferation of cancer cells, such as in patients suffering from cancer. In addition to the compounds themselves, the invention provides pharmaceutical compositions of the compounds and method of treatment using the compounds.

28 Claims, 4 Drawing Sheets

3-ARYL-SUBSTITUTED QUINAZOLONES, AND USES THEREOF

RELATED APPLICATIONS

This application is a national stage filing under 35 U.S.C. 371 of International Application PCT/US2006/049172, filed Dec. 22, 2006, which claims the benefit of U.S. Provisional Application Nos. 60/753,801, filed Dec. 22, 2005, and 60/833,855, filed Jul. 27, 2006, the contents of which are incorporated herein by reference in their entirety. International Application PCT/US2006/049172 was published under PCT Article 21(2) in English.

BACKGROUND OF THE INVENTION

Many drugs administered to treat a disease are targeted against general differences between a diseased cell and a normal cell. For example, paclitaxel, which is used to treat ovarian and breast cancer and inhibits microtubule function, is thought to exhibit tumor cell specificity based on the greater rate of proliferation of tumor cells relative to normal cells (Miller and Ojima, *Chem. Rec.* 1:195-211, 2002). However, despite this consensus view, paclitaxel's in vitro activity varies widely across tumor cell lines (Weinstein et al., *Science* 275:343-349, 1997), indicating that genetic factors can modify sensitivity of tumor cells to paclitaxel and that the responsiveness of tumor cells is not simply determined by their rate of proliferation.

Molecularly targeted therapeutics represent a promising new approach to anti-cancer drug discovery (Shawver et al., *Cancer Cell* 1: 117-23, 2002). Using this approach, small molecules are designed to inhibit directly the very oncogenic proteins that are mutated or overexpressed in specific tumor cell types. By targeting specific molecular defects found within tumor cells, this approach may ultimately yield therapies tailored to each tumor's genetic makeup. Two recent examples of successful molecularly targeted anti-cancer therapeutics are Gleevec (imatinib mesylate), an inhibitor of the breakpoint cluster region-abelsen kinase (BCR-ABL) oncoprotein found in Philadelphia chromosome-positive chronic myelogenous leukemia (Capdeville et al., *Nat Rev Drug Discov* 1: 493-502, 2002) and Herceptin (trastuzumab), a monoclonal antibody targeted against the HER2/NEU oncoprotein found in metastatic breast cancers (Mokbel and Hassanally, *Curr Med Res Opin* 17: 51-9, 2001).

A complementary strategy involves searching for genotype-selective anti-tumor agents that become lethal to tumor cells only in the presence of specific oncoproteins or in the absence of specific tumor suppressors. Such genotype-selective compounds might target oncoproteins directly or they might target other critical proteins involved in oncoprotein-linked signaling networks. Compounds that have been reported to display synthetic lethality include (i) the rapamycin analog CCI-779 in myeloma cells lacking PTEN (Shi et al., *Cancer Res* 62: 5027-34, 2002), (ii) Gleevec in BCR-ABL-transformed cells (Druker et al., *Nat Med* 2: 561-6, 1996) and (iii) a variety of less well-characterized compounds (Stockwell et al., *Chem Biol* 6: 71-83, 1999; Torrance et al., *Nat Biotechnol* 19: 940-5, 2001).

Despite the research discussed above, there remains a significant need to develop and/or identify compounds that selectively target tumor cells.

SUMMARY OF THE INVENTION

A number of compounds/agents/drugs useful for treating or preventing cancer (e.g., tumors or leukemia that may be characterized by Ras pathway activation as a result of mutations in BRAF, HRAS, NRAS or KRAS among others) in an individual, such as a human in need of treatment or prevention, have been identified. As used herein, the terms "agent" and "drug" are used interchangeably; they can be compounds or molecules.

In one embodiment, the invention provides a compound represented by Structural Formula (I):

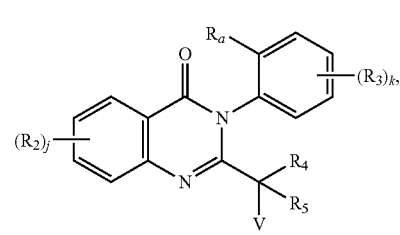

or a pharmaceutically acceptable salt thereof, where:

$R_a$ is a halogen, substituted or unsubstituted alkyl, substituted or unsubstituted alkenyl, substituted or unsubstituted alkynyl, substituted or unsubstituted aryl-O—, substituted or unsubstituted alkyl-O—, substituted or unsubstituted alkenyl-O— or substituted or unsubstituted alkynyl-O—, where alkyl, alkenyl and alkynyl are optionally interrupted by NR, O or $S(O)_n$;

each $R_2$ is independently selected from the group consisting of halogen, substituted or unsubstituted alkyl, substituted or unsubstituted aryl, substituted or unsubstituted non-aromatic heterocyclic, —CN, —COOR', —CON(R)$_2$, —NRC(O)R, —SO$_2$N(R)$_2$, —N(R)$_2$, —NO$_2$, —OH and —OR';

each $R_3$ is independently selected from the group consisting of halogen, substituted or unsubstituted alkyl, substituted or unsubstituted aryl, substituted or unsubstituted non-aromatic heterocyclic, —CN, —COOR', —CON(R)$_2$, —NRC(O)R, —SO$_2$N(R)$_2$, —N(R)$_2$, —NO$_2$, —OH and —OR';

$R_4$ and $R_5$ are independently selected from the group consisting of —H, substituted or unsubstituted alkyl, substituted or unsubstituted alkenyl, substituted or unsubstituted alkynyl, substituted or unsubstituted non-aromatic heterocyclic and substituted or unsubstituted aryl, where alkyl, alkenyl and alkynyl are optionally interrupted by NR, O or $S(O)_n$; or $R_4$ and $R_5$ taken together form a carbocyclic or heterocyclic group;

V is —NH-L-A-Q or

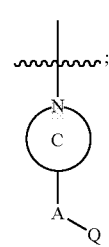

Ring C is a substituted or unsubstituted heterocyclic aromatic or non-aromatic ring;

A is NR or O; or A is a covalent bond;

L is a substituted or unsubstituted hydrocarbyl group optionally interrupted by one or more heteroatoms selected from N, O and S;

Q is selected from the group consisting of —R, —C(O)R', —C(O)N(R)₂, —C(O)OR' and —S(O)₂R';

each R is independently —H, substituted or unsubstituted alkyl, substituted or unsubstituted alkenyl, substituted or unsubstituted alkynyl, substituted or unsubstituted aryl or substituted or unsubstituted non-aromatic heterocyclic;

each R' is independently a substituted or unsubstituted alkyl, substituted or unsubstituted alkenyl, substituted or unsubstituted alkynyl group, substituted or unsubstituted non-aromatic heterocyclic or substituted or unsubstituted aryl group;

j is an integer from 0 to 4;

k is an integer from 0 to 4, provided that at least one of j and k is an integer from 1 to 4; and each n is independently 0, 1 or 2.

In another embodiment, the invention provides a compound represented by Structural Formula (II):

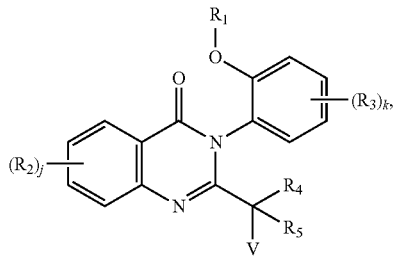

(II)

or a pharmaceutically acceptable salt thereof, where:

$R_1$ is a substituted or unsubstituted alkyl, substituted or unsubstituted alkenyl or substituted or unsubstituted alkynyl group, each of which is optionally interrupted by NR, O or $S(O)_n$;

each $R_2$ is independently selected from the group consisting of halogen, substituted or unsubstituted alkyl, substituted or unsubstituted aryl, substituted or unsubstituted non-aromatic heterocyclic, —CN, —COOR', —CON(R)₂, —NRC(O)R, —SO₂N(R)₂, —N(R)₂, —NO₂, —OH and —OR';

each $R_3$ is independently selected from the group consisting of halogen, substituted or unsubstituted alkyl, substituted or unsubstituted aryl, substituted or unsubstituted non-aromatic heterocyclic, —CN, —COOR', —CON(R)₂, —NRC(O)R, —SO₂N(R)₂, —N(R)₂, —NO₂, —OH and —OR';

$R_4$ and $R_5$ are independently selected from the group consisting of —H, substituted or unsubstituted alkyl, substituted or unsubstituted alkenyl, substituted or unsubstituted alkynyl, substituted or unsubstituted non-aromatic heterocyclic and substituted or unsubstituted aryl, where alkyl, alkenyl and alkynyl are optionally interrupted by NR, O or $S(O)_n$; or $R_4$ and $R_5$ taken together form a carbocyclic or heterocyclic group;

V is —NH-L-A-Q or

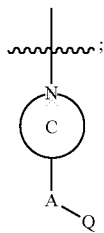

Ring C is a substituted or unsubstituted heterocyclic aromatic or non-aromatic ring;

A is NR or O; or A is a covalent bond;

L is a substituted or unsubstituted hydrocarbyl group optionally interrupted by one or more heteroatoms selected from N, O and S;

Q is selected from the group consisting of —R, —C(O)R', —C(O)N(R)₂, —C(O)OR' and —S(O)₂R';

each R is independently —H, substituted or unsubstituted alkyl, substituted or unsubstituted alkenyl, substituted or unsubstituted alkynyl, substituted or unsubstituted aryl or substituted or unsubstituted non-aromatic heterocyclic;

each R' is independently a substituted or unsubstituted alkyl, substituted or unsubstituted alkenyl, substituted or unsubstituted alkynyl group, substituted or unsubstituted non-aromatic heterocyclic or substituted or unsubstituted aryl group;

j is an integer from 0 to 4;

k is an integer from 0 to 4, provided that at least one of j and k is an integer from 1 to 4; and each n is independently 0, 1 or 2.

The compounds of the invention can be formulated with a pharmaceutically acceptable carrier as pharmaceutical compositions.

In further aspects of the invention, the invention relates to compounds disclosed herein that selectively kill or inhibit the growth of (are toxic to) tumor cells.

In another embodiment, the present invention provides methods of treating a condition in a mammal, comprising administering to the mammal a therapeutically effective amount of a compound of the invention.

Suitable agents can have the recited activity in the existing form or after complete or partial metabolism.

In certain aspects, the compound kills the cells by an apoptotic or non-apoptotic mechanism.

In certain aspects, the cells have enhanced Ras pathway activity (e.g., RasV12).

In certain aspects, the condition is cancer.

Another aspect of the invention provides a method of killing a cell, promoting cell death or inhibiting cellular proliferation, comprising administering to the cell an effective amount of a compound of the invention. Suitable agents can have the recited activity in the existing form or after complete or partial metabolism. In certain embodiments, the cell is a cancer cell.

In one embodiment, the present invention is a method of reducing the growth rate of a tumor, comprising administering an amount of a therapeutic agent sufficient to reduce the growth rate of the tumor, where the therapeutic agent is a compound of the invention. Suitable agents can have the recited activity in the existing form or after complete or partial metabolism.

In one aspect, the invention is a method for treating a patient suffering from a cancer, comprising administering to the patient an effective amount of a compound of the invention. Suitable agents can have the recited activity in the existing form or after complete or partial metabolism.

In another aspect, the invention is a method of increasing sensitivity of a tumor cell to a chemotherapeutic agent (e.g., additively or synergistically), where a tumor cell is contacted with a compound disclosed herein. In a related aspect, the invention is a method of reducing the sensitivity of a normal cell to a chemotherapeutic agent, where a normal cell is contacted with a compound disclosed herein.

In one embodiment, the invention is a method of identifying patients which are likely to respond to treatment with compounds of the invention. Using standard characterization methods known in the art, patients identified as possessing neoplasias displaying one or more of the following attributes would be expected to be responsive: aberrant Ras signaling pathway activity as characterized by activation of one or more pathway members (e.g. phosphorylated Erk1/2, phosphorylated MEK etc.), and/or gene expression profile and/or sensitivity of a cell line of similar or identical genotype to exposure of compounds of the invention either in vitro or in vivo.

In yet another embodiment, the invention is a method of conducting a pharmaceutical business, which includes:

(a) identifying a candidate therapeutic agent for inhibiting cell proliferation, where the candidate therapeutic agent is a compound disclosed herein, (b) conducting therapeutic profiling of the candidate therapeutic agent identified in step (a) for efficacy and toxicity in animals; and (c) formulating a pharmaceutical preparation including one or more the candidate therapeutic agent identified in step (b) as having an acceptable therapeutic profile.

Instead of or in addition to one or both of steps (b) and (c), the method can include licensing to a third party the rights for further development of the candidate therapeutic agent. In a further embodiment, the method of conducting a drug discovery business comprises establishing a distribution system for distributing the pharmaceutical preparation for sale. Optionally, a sales group is established for marketing the pharmaceutical preparation.

The present invention further provides packaged pharmaceuticals. In one embodiment, the packaged pharmaceutical comprises: (i) a therapeutically effective amount of a compound disclosed herein; and (ii) instructions and/or a label for administration of the agent for the treatment of patients having cancer. The instruction or label may be stored on an electronic medium such as CD, DVD, floppy disk, memory card, etc, which may be readable by a computer.

The present invention further provides use of a compound disclosed herein in the manufacture of a medicament for the treatment of cancer.

In certain embodiments, the methods of the invention further comprise conjointly administering one or more agents, such as chemotherapeutic agents that typically kill the cells through an apoptotic mechanism. Agents suitable for use in reducing the growth rate of a tumor and in treating a patient suffering from cancer include, but are not limited to, small organic molecules, peptides, proteins, peptidomimetics, nucleic acids, antibodies and combinations thereof.

It is contemplated that all embodiments of the invention can be combined with one or more other embodiments, even those described under different aspects of the invention.

DETAILED DESCRIPTION OF THE INVENTION

Figure 1:
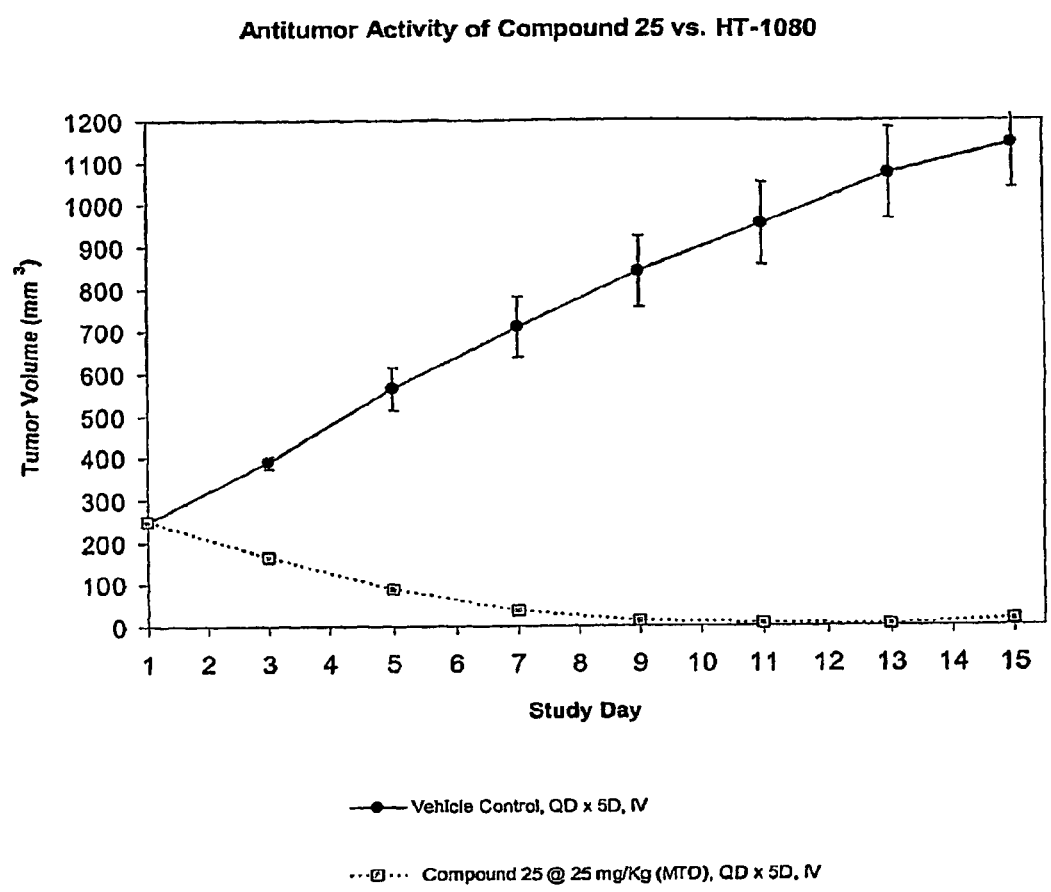
FIG. 1 shows the inhibition in growth of a HT-1080 cell xenograft caused by Compound 25.

The present invention also provides compounds represented by Structural Formula (I), where the compounds are suitable for use in the methods and compositions disclosed herein:

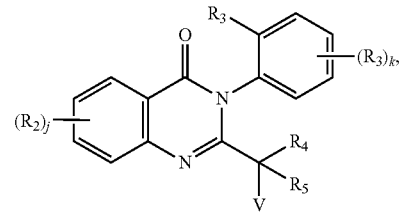

or a pharmaceutically acceptable salt thereof, where:

$R_a$ is a halogen, substituted or unsubstituted alkyl, substituted or unsubstituted alkenyl, substituted or unsubstituted alkynyl, substituted or unsubstituted aryl-O—, substituted or unsubstituted alkyl-O—, substituted or unsubstituted alkenyl-O— or substituted or unsubstituted alkynyl-O—, where alkyl, alkenyl and alkynyl are optionally interrupted by NR, O or $S(O)_n$;

each $R_2$ is independently selected from the group consisting of halogen, substituted or unsubstituted alkyl, substituted or unsubstituted aryl, substituted or unsubstituted non-aromatic heterocyclic, —CN, —COOR', —CON(R)$_2$, —NRC(O)R, —SO$_2$N(R)$_2$, —N(R)$_2$, —NO$_2$, —OH and —OR';

each $R_3$ is independently selected from the group consisting of halogen, substituted or unsubstituted alkyl, substituted or unsubstituted aryl, substituted or unsubstituted non-aromatic heterocyclic, —CN, —COOR', —CON(R)$_2$, —NRC(O)R, —SO$_2$N(R)$_2$, —N(R)$_2$, —NO$_2$, —OH and —OR';

$R_4$ and $R_5$ are independently selected from the group consisting of —H, substituted or unsubstituted alkyl, substituted or unsubstituted alkenyl, substituted or unsubstituted alkynyl, substituted or unsubstituted non-aromatic heterocyclic and substituted or unsubstituted aryl, where alkyl, alkenyl and alkynyl are optionally interrupted by NR, O or $S(O)_n$; or $R_4$ and $R_5$ taken together form a carbocyclic or heterocyclic group;

V is —NH-L-A-Q or

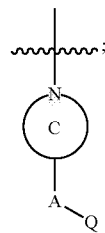

Ring C is a substituted or unsubstituted heterocyclic aromatic or non-aromatic ring;

A is NR or O; or A is a covalent bond;

L is a substituted or unsubstituted hydrocarbyl group optionally interrupted by one or more heteroatoms selected from N, O and S;

Q is selected from the group consisting of —R, —C(O)R', —C(O)N(R)$_2$, —C(O)OR' and —S(O)$_2$R';

each R is independently —H, substituted or unsubstituted alkyl, substituted or unsubstituted alkenyl, substituted or unsubstituted alkynyl, substituted or unsubstituted aryl or substituted or unsubstituted non-aromatic heterocyclic;

each R' is independently a substituted or unsubstituted alkyl, substituted or unsubstituted alkenyl, substituted or unsubstituted alkynyl group, substituted or unsubstituted non-aromatic heterocyclic or substituted or unsubstituted aryl group;

j is an integer from 0 to 4;

k is an integer from 0 to 4, provided that at least one of j and k is an integer from 1 to 4; and each n is independently 0, 1 or 2.

For certain compounds of the invention, V is

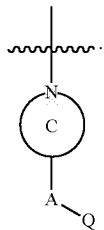

Suitable examples of V encompassed by the above structure include

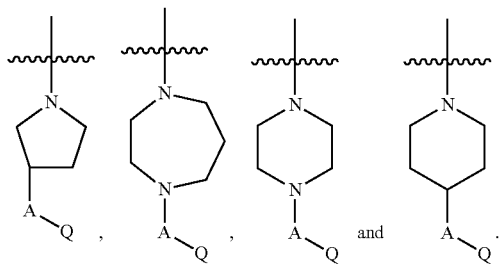

When V is represented by one of these structures, A is typically a covalent bond or NR. Particularly suitable examples of V are

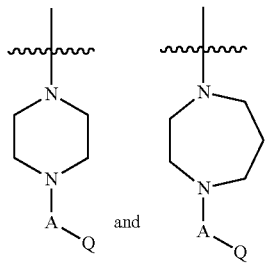

where A is a covalent bond; and

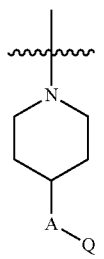

where A is NR.

In certain embodiments, A is a covalent bond and Q is —R. When Q is —R, Q is typically —H or a substituted or unsubstituted alkyl group (e.g., methyl, ethyl). In certain such embodiments, V

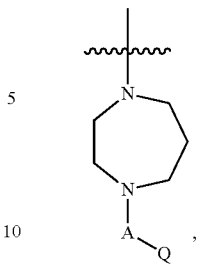

is A is a covalent bond and Q is —H, methyl or ethyl, particularly methyl.

In certain embodiments, the substituent -Q in compounds of the invention, particularly compounds where V is as represented above is an acyl group. Acyl groups typically are represented by —C(O)R', where R' is as defined above. In certain embodiments, R' in —C(O)R' is a substituted or unsubstituted aryl or aryloxyalkyl group, particularly a substituted or unsubstituted phenyl or phenyloxyalkyl group such as a substituted or unsubstituted phenyloxymethyl group. Suitable substituents for the phenyl group include $C_{1-6}$alkyl, $CF_3$, hydroxyl, $C_{1-4}$alkoxy, aryl, aryloxy, halogen, —N(R)$_2$, nitro, carboxylic acid, carboxylic ester, and sulfonyl. Suitable substituents for the phenyloxymethyl group include halogens, particularly chlorine. Chlorine, when present, is preferably at the 4-position of the phenyl ring, to produce a -Q group as shown below:

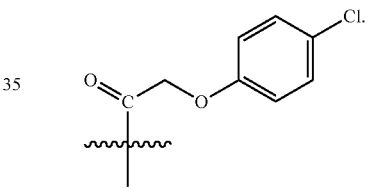

In compounds where V is represented by —NH-L-A-Q, L is typically a substituted or unsubstituted alkylene or poly (alkylene glycol) (e.g., poly(ethylene glycol), poly(propylene glycol). Examples of suitable alkylene are represented by —(CH$_2$)$_j$—, where j is an integer from 1 to 6, such as 2 to 4. Poly(alkylene glycols) are generally 2- or 3-mers.

$R_4$ and $R_5$ are typically independently —H or a substituted or unsubstituted alkyl group (e.g., alkyl, alkoxyalkyl, mono- or dialkylaminoalkyl, aralkyl), particularly when V (including A and Q) has the values described above. More typically, $R_4$ and $R_5$ are independently a substituted or unsubstituted $C_1$-$C_4$ alkyl group, particularly methyl.

$R_1$ is typically a substituted or unsubstituted alkyl group, particularly an unsubstituted $C_1$-$C_4$ alkyl group (e.g., methyl, ethyl, n-propyl, i-propyl, n-butyl, s-butyl, t-butyl). In one example, $R_1$ is typically a substituted or unsubstituted alkyl group when $R_4$, $R_5$, and V have the values described above.

In certain embodiments, j is 1, 2, 3 or 4, such as when k is 0. In certain embodiments, k is 1, 2, 3 or 4, such as when j is 0. In certain embodiments, j is an integer from 1 to 4 and k is an integer from 1 to 4. For example, j is 1 and k is 1, j is 1 and k is 2, j is 1 and k is 3, j is 1 and k is 4, j is 2 and k is 1, j is 2 and k is 2, j is 2 and k is 3, j is 2 and k is 4, j is 3 and k is 1, j is 3 and k is 2, j is 3 and k is 3, j is 3 and k is 4, j is 4 and k is 1, j is 4 and k is 2, j is 4 and k is 3, or j is 4 and k is 4.

When one or more $R_2$ and/or $R_3$ substituent groups are present, they are generally independently selected from the group consisting of polar substituted alkyl, polar substituted alkoxy, polar substituted carbocyclic aryl, substituted or unsubstituted heteroaryl (e.g., nitrogen-containing heteroaryl such as imidazolyl, oxazolyl, thiazolyl, pyridinyl, pyrimidinyl, triazolyl) and substituted or unsubstituted non-aromatic heterocyclic (e.g., pyrrazolyl, piperadinyl, piperazinyl, morpholinyl, homopiperazinyl). Advantageously, these groups improve the water solubility of the compound. Particularly suitable polar substituents include amino, amido, guanidino, —SO$_3$H, —PO$_3$H, —OH and —COOH (including esters that hydrolyze to —COOH), including salts thereof. Other suitable substituents include nitro, halogens such as chlorine, bromine and iodine, and halogen-substituted alkyl and alkoxy groups (e.g., —CF$_3$, —OCF$_3$).

Additional suitable values for R$_2$ and/or R$_3$ include —NRC(O)R and —N(R)$_2$, particularly —NHC(O)R and —NHR. For —NHC(O)R and —NHR, R is typically —H or a substituted alkyl group. The substituents on such alkyl groups are advantageously groups that are able to react with another functional group to form a covalent bond, such as an amine, carboxylic acid, acid halide, halogen or the like. Preferably, R is an aminoalkyl (e.g., where the alkyl is typically C$_3$-C$_6$) when R$_2$ and/or R$_3$ is —NHC(O)R or —NHR or R is —H when R$_2$ and/or R$_3$ is —NHR. Examples of R$_2$ and/or R$_3$ include —NH$_2$, —NHC(O)(CH$_2$)$_3$NH$_2$ and —NH(CH$_2$)$_6$NH$_2$.

In certain embodiment, compounds of Structural Formula (I) are represented by the following particular structures:

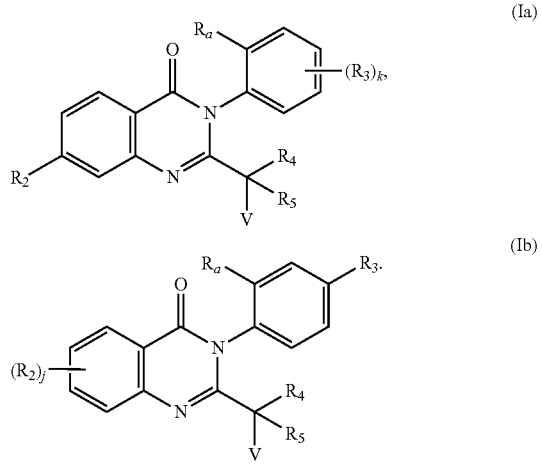

In Structural Formula (Ia), R$_2$ is typically —NHR (e.g., —NH$_2$) and R$_a$ is typically alkoxy (e.g., methoxy, ethoxy). In Structural Formula (Ib), R$_3$ is typically a halogen or —OCF$_3$ and R$_a$ is typically a halogen or alkoxy (e.g., methoxy, ethoxy). In certain embodiments, R$_3$ in Structural Formula (Ia) is present in the same location as R$_3$ in Structural Formula (Ib).

Particularly suitable compounds of the invention have one or more of the following features: (1) V is 4-piperazinyl, 4-homopiperazinyl, 4-methylhomopiperazinyl or 4-(4-chlorophenoxyacetyl)piperazinyl, preferably 4-methylhomopiperazinyl; (2) R$_4$ is —H or an unsubstituted alkyl group, preferably —H or methyl; (3) R$_5$ is —H or an unsubstituted alkyl group, preferably —H or methyl; (4) R$_a$ is an unsubstituted alkyl-O— group, preferably ethyl-O— (i.e., ethoxy); and (5) at least one of R$_2$ and R$_3$ is a group that enhances water solubility (e.g, —NH$_2$), —NO$_2$, —OCF$_3$ and/or a halogen. Examples of such suitable compounds have feature (1); features (1) and (2); features (1)-(3); features (1)-(4); or features (1)-(5).

The present invention also provides compounds represented by Structural Formula (II), where the compounds are suitable for use in the methods and compositions disclosed herein:

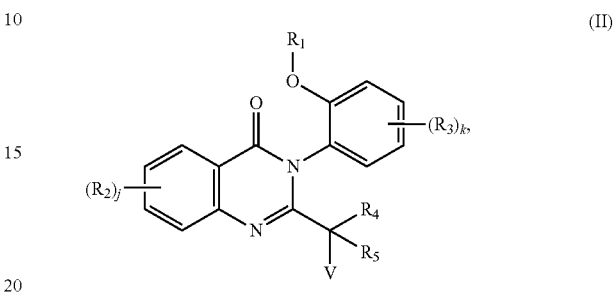

or a pharmaceutically acceptable salt thereof, where:

R$_1$ is a substituted or unsubstituted alkyl, substituted or unsubstituted alkenyl or substituted or unsubstituted alkynyl group, each of which is optionally interrupted by NR, O or S(O)$_n$;

each R$_2$ is independently selected from the group consisting of halogen, substituted or unsubstituted alkyl, substituted or unsubstituted aryl, substituted or unsubstituted non-aromatic heterocyclic, —CN, —COOR', —CON(R)$_2$, —NRC(O)R, —SO$_2$N(R)$_2$, —N(R)$_2$, —NO$_2$, —OH and —OR' (e.g., halogen, substituted or unsubstituted alkyl, substituted or unsubstituted aryl, substituted or unsubstituted non-aromatic heterocyclic, —CN, —COOR', —CON(R)$_2$, —SO$_2$N(R)$_2$, —OH and —OR');

each R$_3$ is independently selected from the group consisting of halogen, substituted or unsubstituted alkyl, substituted or unsubstituted aryl, substituted or unsubstituted non-aromatic heterocyclic, —CN, —COOR', —CON(R)$_2$, —NRC(O)R, —SO$_2$N(R)$_2$, —N(R)$_2$, —NO$_2$, —OH and —OR' (e.g., halogen, substituted or unsubstituted alkyl, substituted or unsubstituted aryl, substituted or unsubstituted non-aromatic heterocyclic, —CN, —COOR', —CON(R)$_2$, —SO$_2$N(R)$_2$, —OH and —OR');

R$_4$ and R$_5$ are independently selected from the group consisting of —H, substituted or unsubstituted alkyl, substituted or unsubstituted alkenyl, substituted or unsubstituted alkynyl, substituted or unsubstituted non-aromatic heterocyclic and substituted or unsubstituted aryl, where alkyl, alkenyl and alkynyl are optionally interrupted by NR, O or S(O)$_n$; or R$_4$ and R$_5$ taken together form a carbocyclic or heterocyclic group;

V is —NH-L-A-Q or

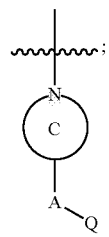

Ring C is a substituted or unsubstituted heterocyclic aromatic or non-aromatic ring;

A is NR or O; or A is a covalent bond;

L is a substituted or unsubstituted hydrocarbyl group optionally interrupted by one or more heteroatoms selected from N, O and S;

Q is selected from the group consisting of —R, —C(O)R', —C(O)N(R)$_2$, —C(O)OR' and —S(O)$_2$R';

each R is independently —H, substituted or unsubstituted alkyl, substituted or unsubstituted alkenyl, substituted or unsubstituted alkynyl, substituted or unsubstituted aryl or substituted or unsubstituted non-aromatic heterocyclic;

each R' is independently a substituted or unsubstituted alkyl, substituted or unsubstituted alkenyl, substituted or unsubstituted alkynyl group, substituted or unsubstituted non-aromatic heterocyclic or substituted or unsubstituted aryl group;

j is an integer from 0 to 4;

k is an integer from 0 to 4, provided that at least one of j and k is an integer from 1 to 4; and each n is independently 0, 1 or 2.

For certain compounds of the invention, V is

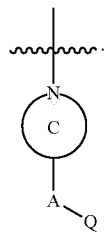

Particularly suitable examples of V are

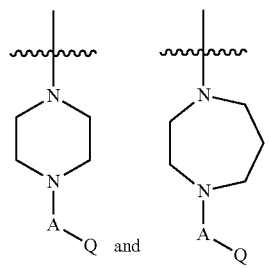

where A is a covalent bond; and

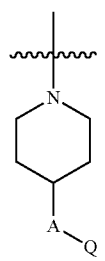

where A is NR.

In certain embodiments, A is a covalent bond and Q is —R. When Q is —R, Q is typically —H or a substituted or unsubstituted alkyl group (e.g., methyl, ethyl). In certain such embodiments, V is

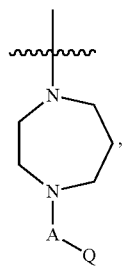

A is a covalent bond and Q is —H, methyl or ethyl, particularly methyl.

In certain embodiments, the substituent -Q in compounds of the invention, particularly compounds where V is as represented above is an acyl group. Acyl groups typically are represented by —C(O)R', where R' is as defined above. In certain embodiments, R' in —C(O)R' is a substituted or unsubstituted aryl or aryloxyalkyl group, particularly a substituted or unsubstituted phenyl or phenyloxyalkyl group such as a substituted or unsubstituted phenyloxymethyl group. Suitable substituents for the phenyl group include $C_{1-6}$alkyl, $CF_3$, hydroxyl, $C_{1-4}$alkoxy, aryl, aryloxy, halogen, —N(R)$_2$, nitro, carboxylic acid, carboxylic ester, and sulfonyl. Suitable substituents for the phenyloxymethyl group include halogens, particularly chlorine. Chlorine, when present, is preferably at the 4-position of the phenyl ring, to produce a -Q group as shown below:

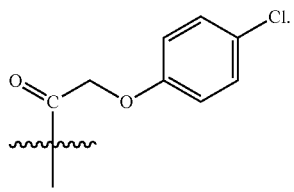 [SMILES: *C(=O)COc1ccc(Cl)cc1]

In compounds where V is represented by —NH-L-A-Q, L is typically a substituted or unsubstituted alkylene or poly(alkylene glycol) (e.g., poly(ethylene glycol), poly(propylene glycol). Examples of suitable alkylene are represented by —(CH$_2$)$_j$—, where j is an integer from 1 to 6, such as 2 to 4. Poly(alkylene glycols) are generally 2- or 3-mers.

$R_4$ and $R_5$ are typically independently —H or a substituted or unsubstituted alkyl group (e.g., alkyl, alkoxyalkyl, mono- or dialkylaminoalkyl, aralkyl), particularly when V (including A and Q) has the values described above. More typically, $R_4$ and $R_5$ are independently —H or a substituted or unsubstituted $C_1$-$C_4$ alkyl group, particularly methyl.

$R_1$ is typically a substituted or unsubstituted alkyl group, particularly an unsubstituted $C_1$-$C_4$ alkyl group (e.g., methyl, ethyl, n-propyl, i-propyl, n-butyl, s-butyl, t-butyl). In one example, $R_1$ is typically a substituted or unsubstituted alkyl group when $R_4$, $R_5$, and V have the values described above.

In certain embodiments, j is 1, 2, 3 or 4, such as when k is 0. In certain embodiments, k is 1, 2, 3 or 4, such as when j is 0. In certain embodiments, j is an integer from 1 to 4 and k is an integer from 1 to 4. For example, j is 1 and k is 1, j is 1 and k is 2, j is 1 and k is 3, j is 1 and k is 4, j is 2 and k is 1, j is 2 and k is 2, j is 2 and k is 3, j is 2 and k is 4, j is 3 and k is 1, j is 3 and k is 2, j is 3 and k is 3, j is 3 and k is 4, j is 4 and k is 1, j is 4 and k is 2, j is 4 and k is 3, or j is 4 and k is 4.

When one or more $R_2$ and/or $R_3$ substituent groups are present, they are generally independently selected from the group consisting of polar substituted alkyl, polar substituted alkoxy, polar substituted carbocyclic aryl, substituted or unsubstituted heteroaryl (e.g., nitrogen-containing heteroaryl such as imidazolyl, oxazolyl, thiazolyl, pyridinyl, pyrimidinyl, triazolyl) and substituted or unsubstituted non-aromatic heterocyclic (e.g., pyrrazolyl, piperadinyl, piperazinyl, morpholinyl, homopiperazinyl). Advantageously, these groups improve the water solubility of the compound. Particularly suitable polar substituents include amino, amido, guanidino, —SO$_3$H, —PO$_3$H, —OH and —COOH (including esters that hydrolyze to —COOH), including salts thereof. Other suitable substituents include nitro, halogens such as chlorine, bromine and iodine, and halogen-substituted alkyl and alkoxy groups (e.g., —CF$_3$, —OCF$_3$).

Additional suitable values for R$_2$ and/or R$_3$ include —NRC(O)R and —N(R)$_2$, particularly —NHC(O)R and —NHR. For —NHC(O)R and —NHR, R is typically —H or a substituted alkyl group. The substituents on such alkyl groups are advantageously groups that are able to react with another functional group to form a covalent bond, such as an amine, carboxylic acid, acid halide, halogen or the like. Preferably, R is an aminoalkyl (e.g., where the alkyl is typically C$_3$-C$_6$) when R$_2$ and/or R$_3$ is —NHC(O)R or —NHR or R is —H when R$_2$ and/or R$_3$ is —NHR. Examples of R$_2$ and/or R$_3$ include —NH$_2$, —NHC(O)(CH$_2$)$_3$NH$_2$ and —NH(CH$_2$)$_6$NH$_2$.

Particularly suitable compounds of the invention have one or more of the following features: (1) V is 4-piperazinyl, 4-homopiperazinyl, 4-methylhomopiperazinyl or 4-(4-chlorophenoxyacetyl)piperazinyl; (2) R$_4$ is an unsubstituted alkyl group, preferably methyl; R$_5$ is —H or an unsubstituted alkyl group, preferably —H or methyl; (4) R$_1$ is an unsubstituted alkyl group, preferably ethyl; and (5) at least one of R$_2$ and R$_3$ is a group that enhances water solubility, —OCF$_3$, —NO$_2$ and/or a halogen. Examples of such suitable compounds have feature (1); features (1) and (2); features (1)-(3); features (1)-(4); or features (1)-(5).

Exemplary compounds include Compounds (1), (2) and (3):

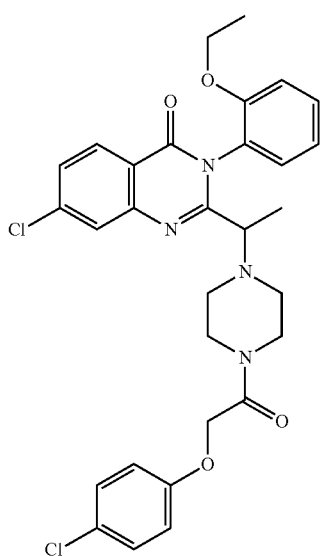

(1)

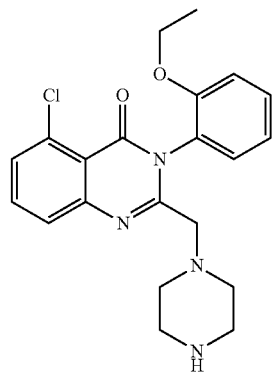

(2)

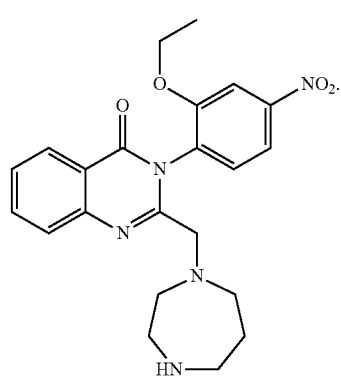

(3)

Additional exemplary compounds include Compounds (4)-(9):

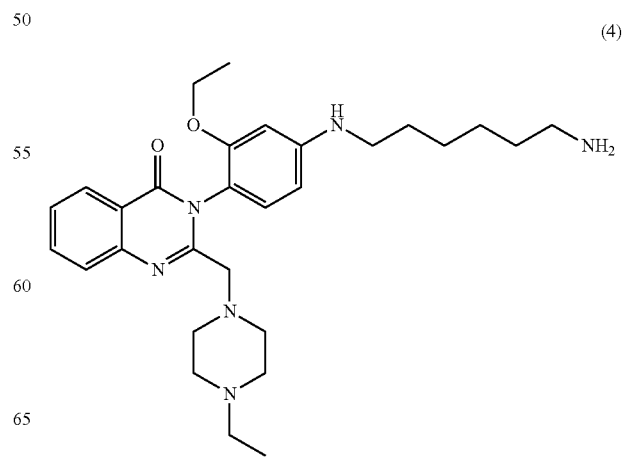

(4)

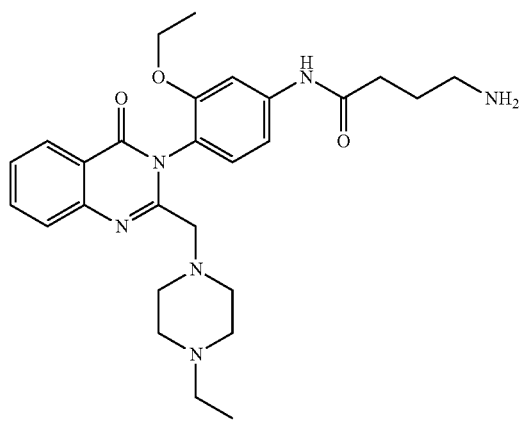
(5)

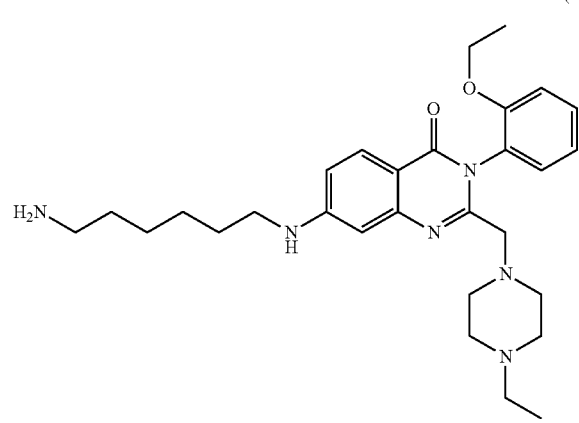
(6)

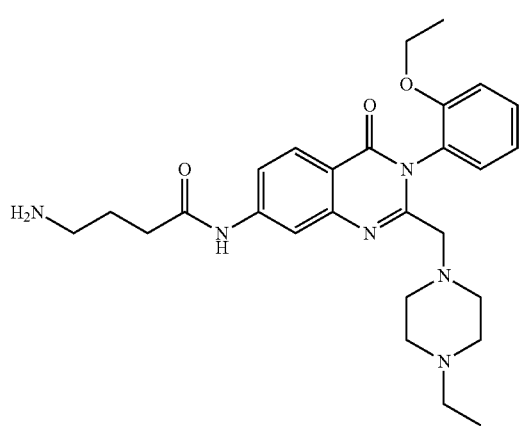
(7)

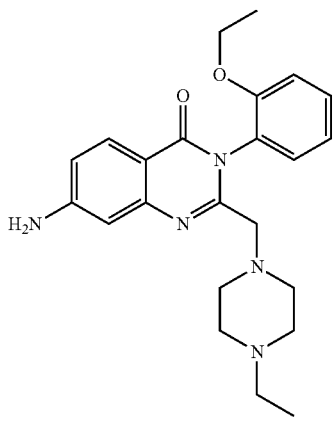
(8)

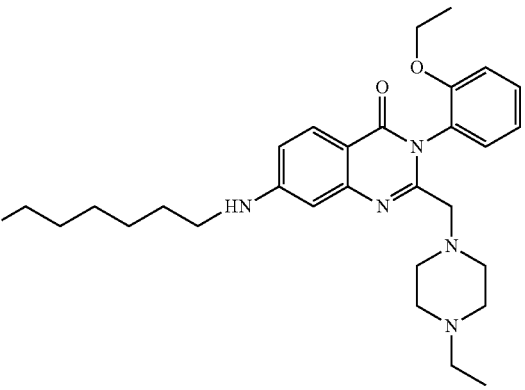
(9)

Further exemplary compounds are shown in the examples.

Compounds included in the invention include enantiomers and diastereomers of the compounds disclosed herein. The invention also includes salts, particularly pharmaceutically acceptable salts of the compounds disclosed herein. In addition, the invention includes solvates, hydrates and polymorph crystalline forms of the compounds disclosed herein.

It is contemplated that all embodiments of the invention can be combined with one or more other embodiments, even those described under different aspects of the invention.

The term "acyl" as used herein includes such moieties as can be represented by the general formula:

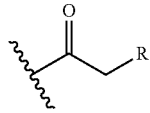

wherein suitable R groups, include, but are not limited to H, alkyl, alkoxy, aralkyl, aryloxy, aryl, heteroaryl, heteroaralkyl, heteroaryloxy, and cycloalkyl, wherein any of these groups may optionally be further appropriately substituted.

The term "hydrocarbyl" refers to substituted or unsubstituted, cyclic or acyclic, saturated or unsaturated hydrocarbon groups. When indicated, hydrocarbyl atoms can be interrupted by one or more heteroatoms such as N, O and S (i.e., the heteroatoms are not at a terminus of the group). The term "alkyl" refers to substituted or unsubstituted saturated hydrocarbon groups, including straight-chain alkyl and branched-chain alkyl groups, including haloalkyl groups such as trifluoromethyl and 2,2,2-trifluoroethyl, etc. $C_0$ alkyl indicates a hydrogen where the group is in a terminal position, a bond if internal. The terms "alkenyl" and "alkynyl" refer to substituted or unsubstituted unsaturated aliphatic groups analogous possible substitution to the alkyls described above, but that contain at least one double or triple bond respectively.

The term "alkoxy" refers to an oxygen having an alkyl group attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "aralkyl", as used herein, refers to an alkyl group substituted with an aryl group.

The term "carbocyclic" as used herein includes 3- to 8-membered substituted or unsubstituted single-ring saturated or unsaturated cyclic aliphatic groups in which each atom of the ring is carbon.

The term "heterocyclic" as used herein includes 3- to 8-membered, preferably 4- to 8-membered, substituted or unsubstituted single-ring cyclic groups in which the ring includes 1 to 3 heteroatoms. Examples of non-aromatic heterocyclic groups include pyrrolidine, piperadine, piperazine, tetrahydrofuran and tetrahydrothiophene.

The term "aryl" as used herein includes 5-, 6-, and 7-membered substituted or unsubstituted single-ring carbocyclic or heterocyclic aromatic groups. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls and/or heterocyclyls. Carbocyclic aryl groups include benzene, naphthalene, phenanthrene, phenol, aniline, and the like. The term "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "small organic molecule" refers to a non-polymeric compound having a molecular weight of less than 2000 amu. Typically, such molecules have a molecular weight of less than 1000 amu, such as less than 500 amu.

Selective Cell Killing

The ability of genotype-selective compounds to serve as molecular probes is based on the premise of chemical genetics, that small molecules can be used to identify proteins and pathways underlying biological effects (Schreiber, 1998, Bioorg. Med. Chem. 6, 1127-1152; Stockwell, 2000, Nat Rev Genet 1, 116-25; Stockwell, 2000, Trends Biotechnol 18, 449-55). For example, the observation that the natural product rapamycin retards cell growth made possible the discovery of the mammalian Target of Rapamycin (mTOR) as a protein that regulates cell growth (Brown et al., 1994, Nature 369, 756-758; Sabatini et al., 1994, Cell 78, 35-43).

A series of human tumor cells have been engineered with defined genetic elements for use in identifying those critical pathways whose disruption leads to a tumorigenic phenotype (Hahn et al., 1999, Nat Med 5, 1164-70; Hahn et al., 2002, Nat Rev Cancer 2, 331-41; Lessnick et al., 2002, Cancer Cell 1, 393-401). It is expected that these experimentally transformed cells will enable identification of genotype-selective agents that exhibit synthetic lethality in the presence of specific cancer-related alleles. Compounds with genotype-selective lethality may serve as molecular probes of signaling networks present in tumor cells, as leads for subsequent development of clinically effective drugs with a favorable therapeutic index and/or as an effective drug.

The invention provides compounds that kill cancer cells, especially genotype-specific cancer cells, such as those with elevated Ras signaling activity.

Thus, one aspect of the invention provides a method to selectively kill cancer cells, especially those with elevated Ras activity, the method comprising administering to a mammalian patient in need of treatment a therapeutically effective amount of a compound disclosed herein.

As is well-known in the art, the constitutive activation of Ras appears to be an important factor for the malignant growth of human cancer cells. Mutations of the RAS proto-oncogenes (H-RAS, N-RAS, K-RAS) are frequent genetic aberrations found in 20% to 30% of all human tumors, although the incidences in tumor type vary greatly (Bos, Cancer Res. 49: 4682-4689, 1989). The highest rates of RAS mutations were detected in adenocarcinomas of the pancreas (90%), the colon (50%), and the lung (30%). In follicular and undifferentiated carcinomas of the thyroid, the incidence of RAS mutations is also considerable (50%). The most commonly observed RAS mutations arise at sites critical for Ras regulation—namely, codons 12, 13, and 61. Each of these mutations results in the abrogation of the normal GTPase activity of Ras. Ras activation is also frequently observed in hematologic malignancies such as myeloid leukemias and multiple myelomas. In about one-third of the myelodysplastic syndromes (MDS) and acute myeloid leukemias (AML), RAS genes are mutationally activated. RAS mutations occur in about 40% of newly diagnosed multiple myeloma patients, and the frequency increases with disease progression.

Cells with an activated Ras pathway can be selectively killed by compounds disclosed herein, likely via an apoptotic mechanism.

Thus, in certain embodiments, cancer cells of certain specific genotypes can be selectively killed by the compounds of the invention. These may include cancers harboring constitutively active Ras mutations or Ras signaling pathway mutations, and enhanced ERK1, MEK1 activity.

In certain other embodiments, the genotype of the target cells may be selectively altered, so that target cells previously not susceptible to compounds of the invention are now susceptible to killing by these compounds.

In certain embodiments, the invention provides a method of selectively killing cancer cells that have elevated Ras pathway activity while protecting relatively normal cells that do not have elevated Ras activity. This can be useful since many cancers harbor the somatic RasV12 or other similar mutations leading to elevated Ras signaling activity in cancer cells, while normal cells in the same patient/individual usually do not have the same RasV12 or other Ras pathway mutations. Compounds of the invention can be used to selectively kill these cancer cells. The subject method would be effective in killing cancer cells since normal cells likely do not have elevated Ras signaling activity.

In some embodiments, the elevated Ras activity is manifested by a constitutively active Ras (N-, H-, or K-Ras) mutation at amino acid positions 12, 13, and/or 61.

In some other embodiments, the elevated Ras activity is manifested by enhanced activity of one or more downstream components of the Ras pathway proteins, including but are not limited to Raf, MEK, MAPK, etc.

In yet other embodiments, cells could be sensitized to the agent(s) through the introduction or expression of a target protein or proteins. Expression can be accomplished by infection of target cells with vectors, such as adenoviral or retroviral vectors expressing the target protein (see below).

Alternatively, the target protein may be directly provided to the target cells. For example, the protein(s) may be introduced into the target cells using various methods known in the art (see details below). In one embodiment, the protein may be provided to the target cell by entrapping it in liposomes bearing positive charges on their surface (e.g., lipofectins) and which are optionally tagged with antibodies against cell surface antigens of the target tissue, e.g., antibodies against a cancer cell surface antigen. In another embodiment, the protein may be provided to the target cells by transcytosis, using any of the "internalizing peptides" capable of mediating this effect, including but not limited to the N-terminal domain of the HIV protein Tat (e.g., residues 1-72 of Tat or a smaller fragment thereof which can promote transcytosis), all or a portion of the Drosophila antenopedia III protein, a sufficient portion of mastoparan, etc. (see below).

In other embodiments, the diminished protein (and/or other other target proteins) may be achieved by delivering an antibody, RNAi (siRNA, short hairpin RNA, etc.), antisense sequence, or small molecule inhibitor specific for such target protein.

Delivery of such antagonists of a protein to a target cell is well known in the art. See, for example, WO04078940A2, EP1439227A1, WO04048545A2, US20040029275A1, WO03076592A2, WO04076674A1, WO9746671A1, all incorporated herein by reference.

Another aspect of the invention provides a conjoint therapeutic method using compounds of the invention and one or more agents or therapies (e.g., radiotherapy) that kill cells via an apoptotic mechanism. Such agents include many of the chemotherapeutic drugs described below.

It is believed that certain proteins have elevated expression levels in cells sensitive to compounds of the invention.

In certain embodiments, target cells are manipulated to express a higher level of a target protein(s) so as to enhance the susceptibility of killing or slowing the rate of proliferation by compounds of the invention.

For example, a target protein may be introduced into the target cells using various methods known in the art (see details below). In one embodiment, the target protein may be provided to the target cell by entrapping it in liposomes bearing positive charges on their surface (e.g., lipofectins) and which are optionally tagged with antibodies against cell surface antigens of the target tissue, e.g., antibodies against a cancer cell surface antigen.

Alternatively, nucleic acids encoding a functional target may be introduced into such target cells, using, for example, adenoviral or retroviral vectors.

In addition, endogenous target protein activity may be stimulated by an agent that either stimulates expression, or suppresses the activity of a target protein inhibitor (transcription or translation inhibitor, or inhibitor that promotes protein turnover in the cell).

In certain aspects, the method of the invention also involves administering an agent that increases the abundance of target protein in the cell. The agent for increasing the abundance of target protein can, for example, include a polynucleotide encoding the protein adapted to be transported into the cell, e.g., fused with a heterologous internalization domain or formulated in liposome preparation.

In certain aspects, the method of the invention also involves administering an agent that decreases the abundance of the target protein in the cell. The agent for decreasing the abundance of the target protein can, for example, inhibit endogenous protein expression, suppress protein expression or enhance the function of a protein inhibitor.

The following sections describe certain exemplary embodiments of the invention, which are contemplated to be capable to combining with one another. In addition, the embodiments are for illustrative purposes only, and should not be construed to be limiting in any respect.

Cell Lines

Previous reports have indicated that it is possible to convert primary human cells into tumorigenic cells by introduction of vectors expressing the hTERT and oncogenic RAS proteins as well as others that disrupt the function of p53, RB and PP2A (Hahn et al., 2002, Mol Cell Biol 22, 2111-23; Hahn et al., 1999, Nature 400, 464-8; Hahn and Weinberg, 2002, Nat Rev Cancer 2, 331-41; Lessnick et al., 2002, Cancer Cell 1, 393-401). A series of engineered human tumorigenic cells and their precursors can be used in the assays described herein. A variety of characteristics of these engineered tumorigenic cells have been reported previously, including their doubling time, their resistance to replicative senescence and crisis in culture, their response to gamma irradiation, their ability to grow in an anchorage-independent fashion and their ability to form tumors in immunodeficient mice (Hahn et al., 1999, supra; Hahn at al., 2002, supra; Lessnick et al., 2002, supra).

Methods of Screening for Genotype-Selective Compounds

As used herein, the terms agent and drug are used interchangeably. As used herein, the term "is toxic to" refers to the ability of an agent or compound to kill or inhibit the growth/proliferation of tumorigenic cells. Large-scale screens include screens wherein hundreds or thousands of compounds are screened in a high-throughput format for selective toxicity to engineered tumorigenic cells. In one embodiment of the invention, selective toxicity is determined by comparing cell viability of test cells, which are tumorigenic cells, and control cells after contact with a candidate agent. An appropriate control is a cell that is the same type of cell as that of test cells except that the control cell is not tumorigenic. For example, control cells may be the parental primary cells from which the test cells are derived. Control cells are contacted with the candidate agent under the same conditions as the test cells. An appropriate control may be run simultaneously, or it may be pre-established (e.g., a pre-established standard or reference). Cell viability may be determined by any of a variety of means known in the art, including the use of dyes such as Sytox, calcein acetoxymethyl ester (calcein AM) and Alamar Blue. In certain embodiments of the invention, a dye such as calcein AM is applied to test and control cells after treatment with a candidate agent. In live cells, calcein AM is cleaved by intracellular esterases, forming the anionic fluorescent derivative calcein, which cannot diffuse out of live cells. Hence, live cells exhibit a green fluorescence when incubated with calcein AM, whereas dead cells do not. The green fluorescence that is exhibited by live cells can be detected and can thereby provide a measurement of cell viability.

In certain embodiments of the invention, an agent that has been identified as one that selectively induces cell death in vitro is further characterized in an animal model. Animal models include mice, rats, rabbits, and monkeys, which can be nontransgenic wildtype) or transgenic animals. The effect of the agent that selectively induces cell death in engineered tumorigenic cells may be assessed in an animal model for any number of effects, such as its ability to selectively induce cell death in tumorigenic cells in the animal and its general toxicity to the animal. For example, the method can comprise further assessing the selective toxicity of an agent (drug) to tumorigenic cells in an appropriate mouse model.

The effect of the agent that induces death in tumorigenic cells may be assessed in an animal model for any number of effects, such as its ability to induce death in tumorigenic cells in the animal and its general toxicity to the animal. For example, the method can comprise further assessing the toxicity of an agent (drug) to tumorigenic cells in an appropriate mouse model. To illustrate, an agent can be further evaluated by using a tumor growth assay which assesses the ability of tested agent to inhibit the growth of established solid tumors in mice. The assay can be performed by implanting tumor cells into the fat pads of nude mice. Tumor cells are then allowed to grow to a certain size before the agents are administered. The volumes of tumors are monitored for a set number of weeks, e.g., three weeks. General health of the tested animals is also monitored during the course of the assay.

An agent that has been identified as one that selectively kills or inhibits the growth/proliferation of tumorigenic cells can be further characterized in cell-based assays to assess its mechanism of action. For example, the agent can be tested in apoptosis assays to assess its ability to induce cell death by means of a pro-apoptotic pathway. In addition, an agent that induces death in tumor cells can be assessed for its ability to induce death in tumorigenic cells by a non-apoptotic pathway. For example, the agent can be tested in apoptosis assays to assess its inability to induce cell death by means of a pro-apoptotic pathway.

If the viability of the test cells is more than that of the control cells in the assays described above, then an agent (drug) that selectively suppresses the cellular toxicity is identified. Control cells are contacted with the candidate agent under the same conditions as the test cells. An appropriate control may be run simultaneously, or it may be pre-established (e.g., a pre-established standard or reference).

Genotype-Selective Compounds of the Invention

Expression of $RAS^{V12}$ leads to the activation of several well-characterized signaling pathways, including the RAF-MEK-MAPK signaling cascade, the phosphatidylinositol 3-kinase (PI3K) signaling pathway and the Ral-guanine dissociation factor pathway (Ral-GDS). Each of these pathways has been implicated in human cancers, and recent work demonstrates that these pathways work in concert in this system of cell transformation (Hamad et al., 2002, Genes Dev 16, 2045-57).

Methods of Identifying Targets for Genotype-Selective Compounds

In certain embodiments, the invention relates to the use of compounds of the invention, also referred to herein as "ligand", to identify targets (also referred to herein as "cellular components" (e.g., proteins, nucleic acids, or lipids) involved in conferring the phenotype of diseased cells.

In one embodiment, the invention provides a method to identify cellular components involved in tumorigenesis, whereby a tumorigenic cell, such as an engineered human tumorigenic cell, tissue, organ, organism or a lysate or an extract thereof is contacted with a subject anti-tumor compound; and after contact, cellular components that interact (directly or indirectly) with a ligand are identified, resulting in identification of cellular components involved in tumorigenesis. In another embodiment, the invention provides a method to identify cellular components involved in tumorigenesis. In this method, (a) a tumorigenic cell, such as an engineered human tumorigenic cell, tissue, organ, organism or a lysate or an extract thereof is contacted with an inhibitor of a ligand and contacted with the ligand; and (b) cellular components that interact (directly or indirectly) with the inhibitor of the ligand are identified, which cellular components are involved in tumorigenesis. The cell can be contacted with the ligand and the inhibitor of the ligand sequentially or simultaneously. Cellular components that interact with the ligand or any agent of the present invention may be identified by known methods.

As described herein, the subject compound (or ligand) of these methods may be created by any chemical method. The ligand may be optionally derivatized with another compound. One advantage of this modification is that the derivatizing compound may be used to facilitate ligand target complex collection or ligand collection, e.g., after separation of ligand and target. Non-limiting examples of derivatizing groups include biotin, fluorescein, digoxygenin, green fluorescent protein, isotopes, polyhistidine, magnetic beads, glutathione S transferase, photoactivatible crosslinkers or any combinations thereof. Derivatizing groups can also be used in conjunction with targets (e.g., an erastin binding protein) in order to facilitate their detection.

According to the present invention, a target (cellular component) may be a naturally occurring biomolecule synthesized in vivo or in vitro. A target may be comprised of amino acids, nucleic acids, sugars, lipids, natural products or any combinations thereof. An advantage of the instant invention is that no prior knowledge of the identity or function of the target is necessary.

The interaction between the ligand and target may be covalent or non-covalent. Optionally, the ligand of a ligand-target pair may or may not display affinity for other targets. The target of a ligand-target pair may or may not display affinity for other ligands.

For example, binding between a ligand and a target can be identified at the protein level using in vitro biochemical methods, including photo-crosslinking, radiolabeled ligand binding, and affinity chromatography (Jakoby W B et al., 1974, Methods in Enzymology 46: 1). Alternatively, small molecules can be immobilized on a suitable solid support or affinity matrix such as an agarose matrix and used to screen extracts of a variety of cell types and organisms. Similarly, the small molecules can be contacted with the cell, tissue, organ, organism or lysate or extract thereof and the solid support can be added later to retrieve the small molecules and associate target proteins.

Expression cloning can be used to test for the target within a small pool of proteins (King R W et. al., 1997, Science 277:973). Peptides (Kieffer et. al., 1992, PNAS 89:12048), nucleoside derivatives (Haushalter K A et. al., 1999, Curr. Biol. 9:174), and drug-bovine serum albumin (drug-BSA) conjugate (Tanaka et. al., 1999, Mol. Pharmacol. 55:356) have been used in expression cloning.

Another useful technique to closely associate ligand binding with DNA encoding the target is phage display. In phage display, which has been predominantly used in the monoclonal antibody field, peptide or protein libraries are created on the viral surface and screened for activity (Smith G P, 1985, Science 228:1315). Phages are panned for the target which is connected to a solid phase (Parmley S F et al., 1988, Gene 73:305). One of the advantages of phage display is that the cDNA is in the phage and thus no separate cloning step is required.

A non-limiting example includes binding reaction conditions where the ligand comprises a marker such as biotin, fluorescein, digoxygenin, green fluorescent protein, radioisotope, histidine tag, a magnetic bead, an enzyme or combinations thereof. In one embodiment of the invention, the targets may be screened in a mechanism based assay, such as an assay to detect ligands which bind to the target. This may include a solid phase or fluid phase binding event with either the ligand or the protein or an indicator of either being detected. Alternatively, the gene encoding the protein with previously undefined function can be transfected with a reporter system (e.g., β-galactosidase, luciferase, or green fluorescent protein) into a cell and screened against the library preferably by a high throughput screening method or with individual members of the library. Other mechanism based binding assays may be used, for example, biochemical assays measuring an effect on enzymatic activity, cell based assays in which the target and a reporter system (e.g., luciferase or β-galactosidase) have been introduced into a cell, and binding assays which detect changes in free energy. Binding assays can be performed with the target fixed to a well, bead or chip or captured by an immobilized antibody or resolved by capillary electrophoresis. The bound ligands may be detected usually using colorimetric or fluorescence or surface plasmon resonance.

In certain embodiments, the present invention further contemplates methods of treating or preventing a disease (e.g., cancer) by modulating the function (e.g., activity or expression) of a target (cellular component) that is identified according to the invention. To illustrate, if a target is identified to promote tumor growth, a therapeutic agent can be used to modify or reduce the function (activity or expression) of the target. Alternatively, if a target is identified to inhibit tumor growth, a therapeutic agent can be used to enhance the function (activity or expression) of the target. The therapeutic agent is a compound of the invention.

Methods of Treatment

In certain embodiments, the invention provides a method to treat or prevent cancer in an individual. The terms "cancer," "tumor," and "neoplasia" are used interchangeably herein. As used herein, a cancer (tumor or neoplasia) is characterized by one or more of the following properties: cell growth is not regulated by the normal biochemical and physical influences in the environment; anaplasia (e.g., lack of normal coordinated cell differentiation); and in some instances, metastasis. Cancer diseases include, for example, anal carcinoma, bladder carcinoma, breast carcinoma, cervix carcinoma, chronic lymphocytic leukemia, chronic myelogenous leukemia, endometrial carcinoma, hairy cell leukemia, head and neck carcinoma, lung (small cell) carcinoma, multiple myeloma, non-Hodgkin's lymphoma, follicular lymphoma, ovarian carcinoma, brain tumors, colorectal carcinoma, hepatocellular carcinoma, Kaposi's sarcoma, lung (non-small cell carcinoma), melanoma, pancreatic carcinoma, prostate carcinoma, renal cell carcinoma, and soft tissue sarcoma. Additional cancer disorders can be found in, for example, Isselbacher et al. (1994) Harrison's Principles of Internal Medicine 1814-1877, herein incorporated by reference.

Typically, the cancers described above and treatable by the methods described herein exhibit deregulated Ras pathway activity. In one embodiment, the cancers described above contain a mutation in the Ras signaling pathway, resulting in elevated Ras signaling activity. For example, the mutation could be a constitutively active mutation in the Ras gene, such as Ras V12. The mutation could also be in any of the Ras-pathway related genes that could result in activation or altered activity of the pathway.

In one embodiment, the invention relates to a method of treating or preventing cancer in an individual, comprising administering to the individual a therapeutically effective amount of a compound that is selectively toxic to an engineered human tumorigenic cell, or a cancer cell of specific genotype (or specifically altered genotype). In certain embodiments, the cancer is characterized by cells comprising an activated RAS pathway. In certain further embodiments, the cancer is characterized by cells expressing SV40 small T oncoprotein, or exhibiting modulations of targets of sT and/or oncogenic RAS.

In a related embodiment, the invention contemplates the practice of the method of the invention in conjunction with other anti-tumor therapies such as conventional chemotherapy directed against solid tumors and for control of establishment of metastases. The administration of the other anti-tumor therapies can be conducted during or after chemotherapy. Such agents are typically formulated with a pharmaceutically acceptable carrier, and can be administered intravenously, orally, bucally, parenterally, by an inhalation spray, by topical application or transdermally. An agent can also be administered by local administration. Preferably, one or more additional agents administered in conjunction with an anti-cancer chemotherapeutic agent (e.g., a compound of the invention) inhibits cancer cells in an additive or synergistic manner compare.

A wide array of conventional compounds has been shown to have anti-tumor activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-tumor compounds induce undesirable side effects. In many cases, when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

Therefore, compounds and pharmaceutical compositions of the present invention may be conjointly administered with a conventional anti-tumor compound. Conventional anti-tumor compounds include, merely to illustrate: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

In other embodiments, compounds and pharmaceutical compositions of the present invention may be conjointly administered with a conventional anti-tumor compound selected from: an EGF-receptor antagonist, arsenic sulfide, adriamycin, cisplatin, carboplatin, cimetidine, carminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, megestrol, methopterin, mitomycin C, ecteinascidin 743, busulfan, carmustine (BCNU), lomustine (CCNU), lovastatin, 1-methyl-4-phenylpyridinium ion, semustine, staurosporine, streptozocin, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenolic acid, daunorubicin, deferoxamine, floxuridine, doxifluridine, raltitrexed, idarubicin, epirubican, pirarubican, zorubicin, mitoxantrone, bleomycin sulfate, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, enediynes, levamisole, aflacon, interferon, interleukins, aldesleukin, filgrastim, sargramostim, rituximab, BCG, tretinoin, betamethosone, gemcitabine hydrochloride, verapamil, VP-16, altretamine, thapsigargin, oxaliplatin, iproplatin, tetraplatin, lobaplatin, DCP, PLD-147, JM118, JM216, JM335, satraplatin, docetaxel, deoxygenated paclitaxel, TL-139, 5'-nor-anhydrovinblastine (hereinafter: 5'-nor-vinblastine), camptothecin, irinotecan (Camptosar, CPT-11), topotecan (Hycamptin), BAY 38-3441, 9-nitrocamptothecin (Orethecin, rubitecan), exatecan (DX-8951), lurtotecan (GI-147211C), gimatecan, homocamptothecins diflomotecan (BN-80915) and 9-aminocamptothecin (IDEC-13'), SN-38, ST1481, karanitecin (BNP1350), indolocarbazoles (e.g., NB-506), protoberberines, intoplicines, idenoisoquinolones, benzo-phenazines or NB-506.

In another related embodiment, the invention contemplates the practice of the method in conjunction with other anti-tumor therapies such as radiation. As used herein, the term "radiation" is intended to include any treatment of a neoplastic cell or subject by photons, neutrons, electrons, or other type of ionizing radiation. Such radiations include, but are not limited to, X-ray, gamma-radiation, or heavy ion particles, such as alpha or beta particles. Additionally, the radiation may be radioactive. The means for irradiating neoplastic cells in a subject are well known in the art and include, for example, external beam therapy, and brachytherapy.

Methods to determine if a cancer (tumor or neoplasia) has been treated are well known to those skilled in the art and include, for example, a decrease in the number of tumor cells (e.g., a decrease in cell proliferation or a decrease in tumor size). It is recognized that the treatment of the present invention may be a lasting and complete response or can encompass a partial or transient clinical response. See for example, Isselbacher et al. (1996) Harrison's Principles of Internal Medicine 13 ed., 1814-1882, incorporated herein by reference.

Assays to test for the sensitization or the enhanced death of tumor cells are well known in the art, including, for example, standard dose response assays that assess cell viability; agarose gel electrophoresis of DNA extractions or flow cytometry to determine DNA fragmentation, a characteristic of cell death; assays that measure the activity of polypeptides involved in apoptosis; and assay for morphological signs of cell death. The details regarding such assays are described elsewhere herein. Other assays include, chromatin assays (e.g., counting the frequency of condensed nuclear chromatin) or drug resistance assays as described in, for example, Lowe et al. (1993) Cell 74:95 7-697, herein incorporated by reference. See also U.S. Pat. No. 5,821,072, also herein incorporated by reference.

Pharmaceutical Compositions

Prospective therapeutic agents can be profiled in order to determine their suitability for inclusion in a pharmaceutical composition. One common measure for such agents is the therapeutic index, which is the ratio of the therapeutic dose to a toxic dose. The thresholds for therapeutic dose (efficacy) and toxic dose can be adjusted as appropriate (e.g., the necessity of a therapeutic response or the need to minimize a toxic response). For example, a therapeutic dose can be the therapeutically effective amount of an agent (relative to treating one or more conditions) and a toxic dose can be a dose that causes death (e.g., an $LD_{50}$) or causes an undesired effect in a proportion of the treated population. Preferably, the therapeutic index of an agent is at least 2, more preferably at least 5, and even more preferably at least 10. Profiling a therapeutic agent can also include measuring the pharmacokinetics of the agent, to determine its bioavailability and/or absorption when administered in various formulations and/or via various routes.

A compound of the present invention can be administered to an individual in need thereof. In certain embodiments, the individual is a mammal such as a human, or a non-human mammal. When administered to an individual, the compound of the invention can be administered as a pharmaceutical composition containing, for example, the compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. In a preferred embodiment, when such pharmaceutical compositions are for human administration, the aqueous solution is pyrogen free, or substantially pyrogen free. The excipients can be chosen, for example, to effect delayed release of an agent or to selectively target one or more cells, tissues or organs.

A pharmaceutically acceptable carrier can contain physiologically acceptable agents that act, for example, to stabilize or to increase the absorption of a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition (preparation) also can be a liposome or other polymer matrix, which can have incorporated therein, for example, a compound of the invention. Liposomes, for example, which consist of phospholipids or other lipids, are nontoxic, physiologically acceptable and metabolizable carriers that are relatively simple to make and administer.

A pharmaceutical composition (preparation) containing a compound of the invention can be administered to a subject by any of a number of routes of administration including, for example, orally; intramuscularly; intravenously; anally; vaginally; parenterally; nasally; intraperitoneally; subcutaneously; and topically. The composition can be administered by injection or by incubation.

In certain embodiments, the compound of the present invention may be used alone or conjointly administered with another type of anti-tumor therapeutic agent. As used herein, the phrase "conjoint administration" refers to any form of administration in combination of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. Thus, an individual who receives such treatment can benefit from a combined effect of different therapeutic compounds.

It is contemplated that the compound of the present invention will be administered to a subject (e.g., a mammal, preferably a human) in a therapeutically effective amount (dose). By "therapeutically effective amount" is meant the concentration of a compound that is sufficient to elicit the desired therapeutic effect (e.g., treatment of a condition, the death of a neoplastic cell). It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. Typically, for a human subject, an effective amount will range from about 0.001 mg/kg of body weight to about 50 mg/kg of body weight. A larger total dose can be delivered by multiple administrations of the agent. Methods to determine efficacy and dosage are known to those skilled in the art. See, for example, Isselbacher et al. (1996) Harrison's Principles of Internal Medicine 13 ed., 1814-1882, herein incorporated by reference.

EXEMPLIFICATION

The invention now being generally described, it will be more readily understood by reference to the following examples, which are included merely for purposes of illustration of certain aspects and embodiments of the present invention, and are not intended to limit the invention.

Example 1

Preparation of 2-(1-(4-(2-(4-chlorophenoxy)acetyl) piperazin-1-yl)ethyl)-7-chloro-3-(2-ethoxyphenyl) quinazolin-4(3H)-one 2-(1-(4-(2-(4-chlorophenoxy)acetyl)piperazin-1-yl) ethyl)-7-chloro-3-(2-ethoxyphenyl)quinazolin-4(3H)-one (Compound 1) was prepared according to the reactions shown in Scheme 1.

Scheme 1

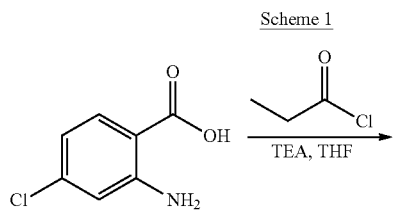

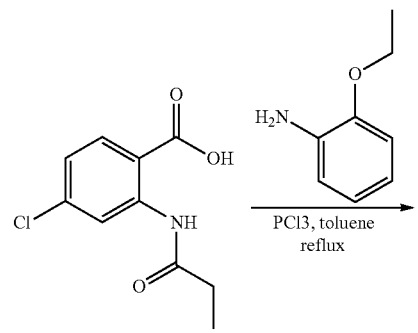

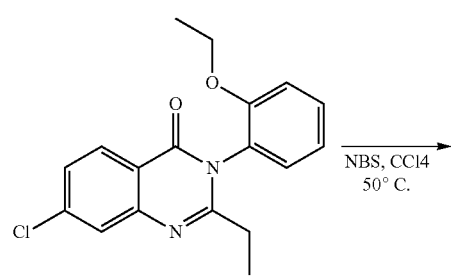

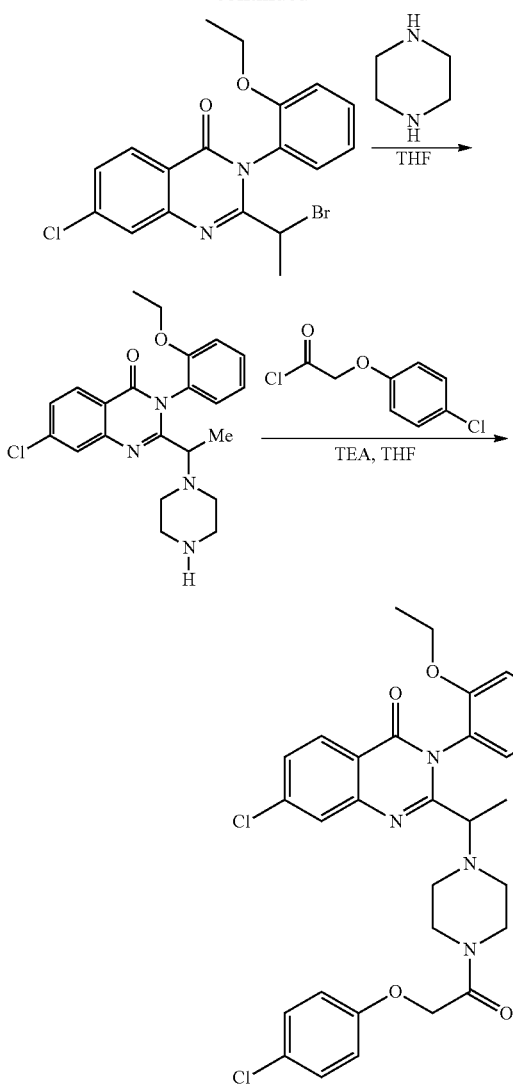
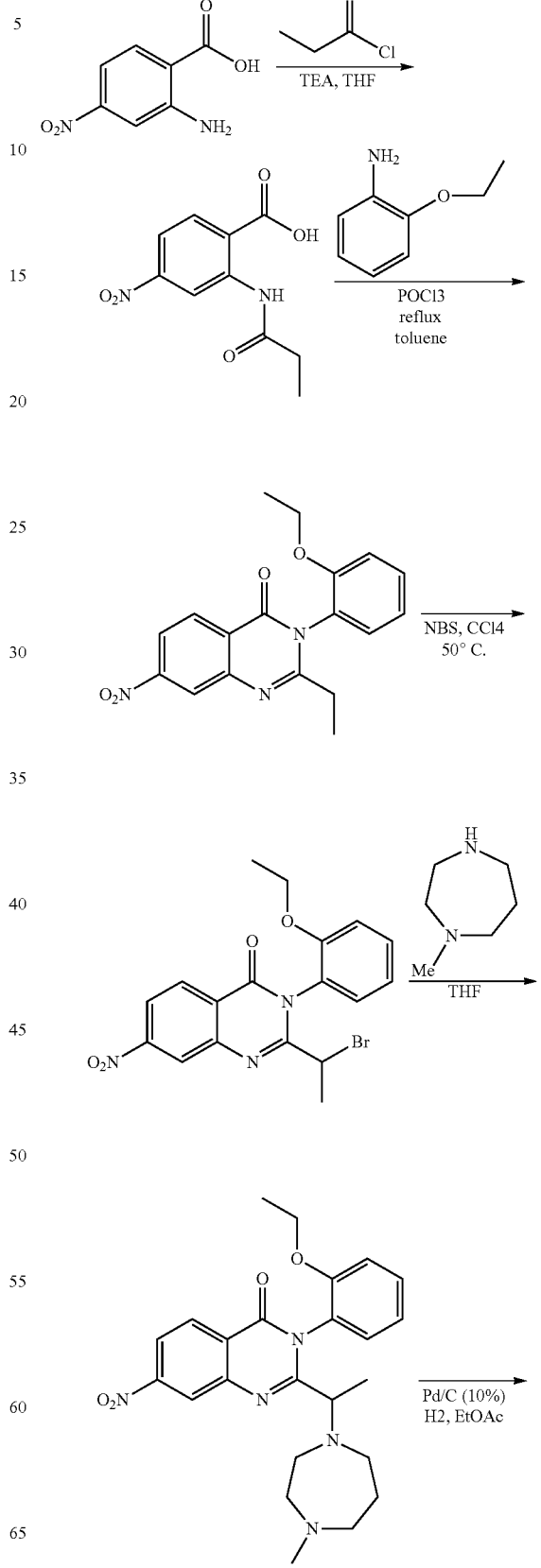

Scheme 2

Briefly, 2-amino-4-chlorobenzoic acid was acylated with propionyl chloride in triethylamine (TEA) and tetrahydrofuran (THF). The acylated compound was refluxed with 2-ethoxyaniline in phosphorus trichloride and toluene to produce 2-ethyl-7-chloro-3-(2-ethoxyphenyl)quinazolin-4(3H)-one. The 2-ethyl-7-chloro-3-(2-ethoxyphenyl)quinazolin-4(3H)-one was brominated with N-bromosuccinimide (NBS) in carbon tetrachloride, the product of which was subsequently reacted with piperazine in THF. The piperazinyl moiety was acylated with 4-chlorophenoxyacetyl chloride in THF and TEA to yield the final product.

Example 2

Preparation of 3-(2-Ethoxyphenyl)-2-[(hexahydro-4-methyl-1H-1,4-diazepin-1-yl)methyl]quinazolin-4(3H)-one 3-(2-Ethoxyphenyl)-2-[(hexahydro-4-methyl-1H-1,4-diazepin-1-yl)methyl]quinazolin-4(3H)-one (Compound 10) was prepared according to the reactions shown in Scheme 2.

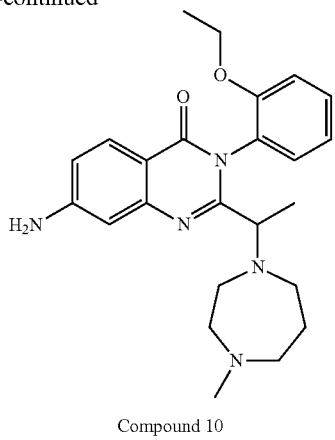

Compound 10

Briefly, 2-amino-4-nitrobenzoic acid was acylated with propionyl chloride in triethylamine (TEA) and tetrahydrofuran (THF). The acylated compound was refluxed with 2-ethoxyaniline in phosphorus oxychloride (POCl3) and toluene to produce 2-ethyl-7-nitro-3-(2-ethoxyphenyl)quinazolin-4(3H)-one. The 2-ethyl-7-nitro-3-(2-ethoxyphenyl)quinazolin-4(3H)-one was brominated with N-bromosuccinimide (NBS) in carbon tetrachloride, the product of which was subsequently reacted with N-methylhomopiperazine in THF. The product of this reaction was subjected to hydrogenation conditions using catalytic amounts of Pd/carbon (10% Pd) to afford Compound 10.

Example 3

Inhibition of Cell Growth by Compound 1

The ability of Compound 1, in DMSO, to inhibit the growth of tumor and normal cells was measured. The compound was assayed by the Sytox primary screen, a phenotypic assay which monitors alterations in cell survival-proliferation as a result of compound treatment. It was devised as high through-put method to identify compounds which specifically alter the growth potential of cells harboring the causative mutations found in cancer patients while not affecting the growth of normal cells. The assay relies upon an inexpensive, simple and reliable readout of a membrane impermeable fluorescent dye (Sytox, from Molecular Probes) which binds to nucleic acid. In healthy cells, no signal is detected because the cell's membrane is intact and the dye will not enter. However, if a cell's membrane is compromised as a result of apoptosis or necrosis, a fluorescent signal proportional to the number of similarly affected cells will be detected. By utilizing a two-step readout (final read in the presence of detergent to permit labeling of all cells), the assay can identify compounds which produce cytostasis, cytotoxicity and/or mitogenesis. The first read or "dead cell" read, provides an estimate of the toxicity of a given compound by indicating the number of dead or dying cells in the culture at the time of assay. The second read or "total cell" read, captures both the cumulative effects of cytoxicity in reducing the size of the cell population as well as any cytostatic or anti-proliferative effects a test compound may exert on the cells in the test population in the absence of toxicity.

Cells were seeded overnight in 96 well plates at densities that without treatment would permit 95% confluence in the wells 72 hours later. The following day, the cells were exposed to test compounds in a dilution series for a period of 48 hours. Following this incubation period, the Sytox reagent was added to the cultures at the manufacturer's recommended concentration and the dead cell fluorescence read was taken. After completion of this measurement, the detergent Saponin was added to each well of the cultures to permeabilize the membranes allowing the Sytox reagent to enter every cell, thereby facilitating measurement of the total number of cells remaining in the culture. For data evaluation, no differentiation was made between compounds which exhibited cytotoxic or cytostatic effects.

Figure 2:
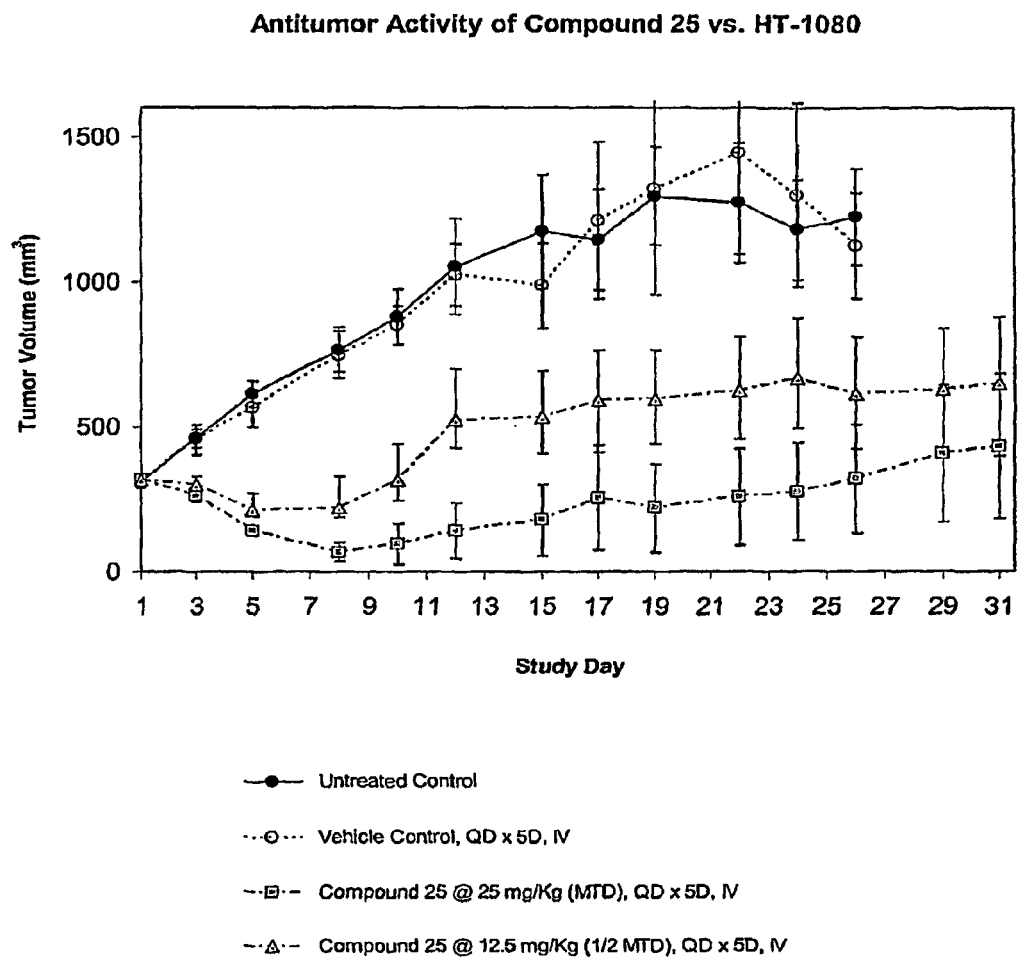
FIG. 2 shows the inhibition in growth of a HT-1080 cell xenograft caused by Compound 25.

The results of the assay are shown in FIG. 2. Compound 1 inhibited the growth of tumor cells with an $IC_{50}$ of about 10 µM.

Figure 3:
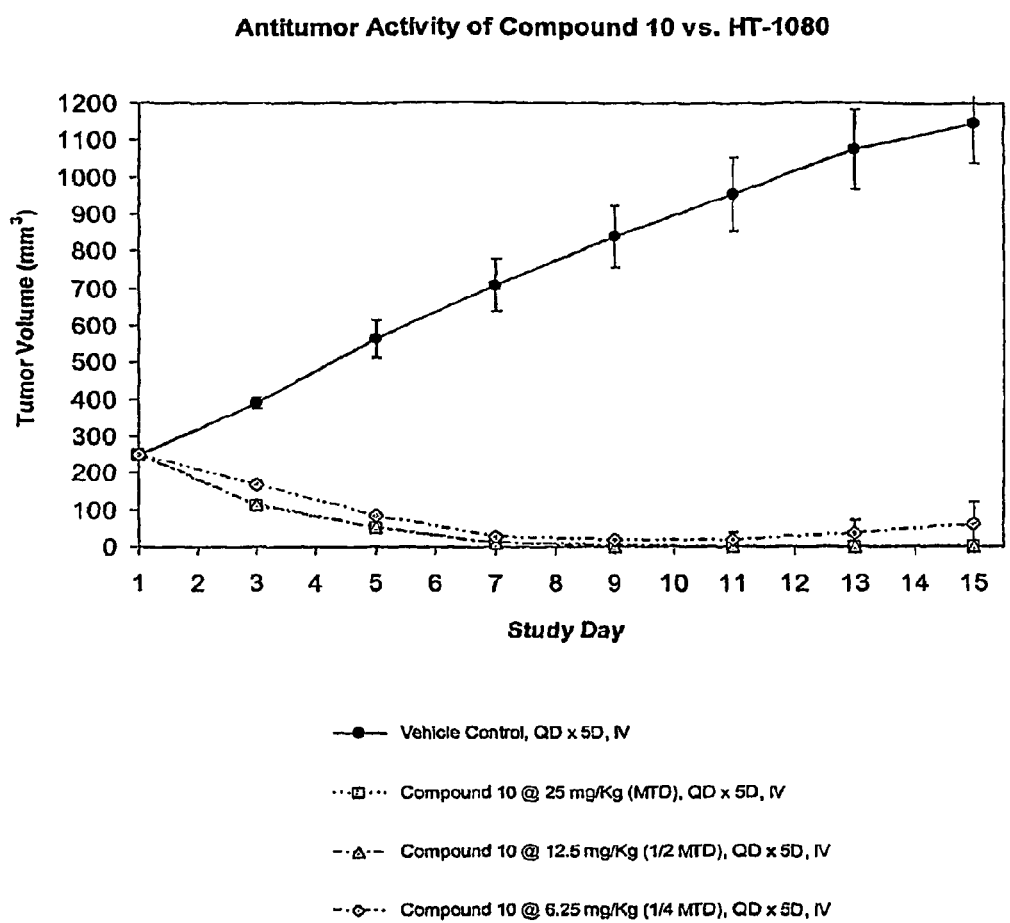
FIG. 3 shows the inhibition in growth of a HT-1080 cell xenograft caused by Compound 10.
Figure 4:
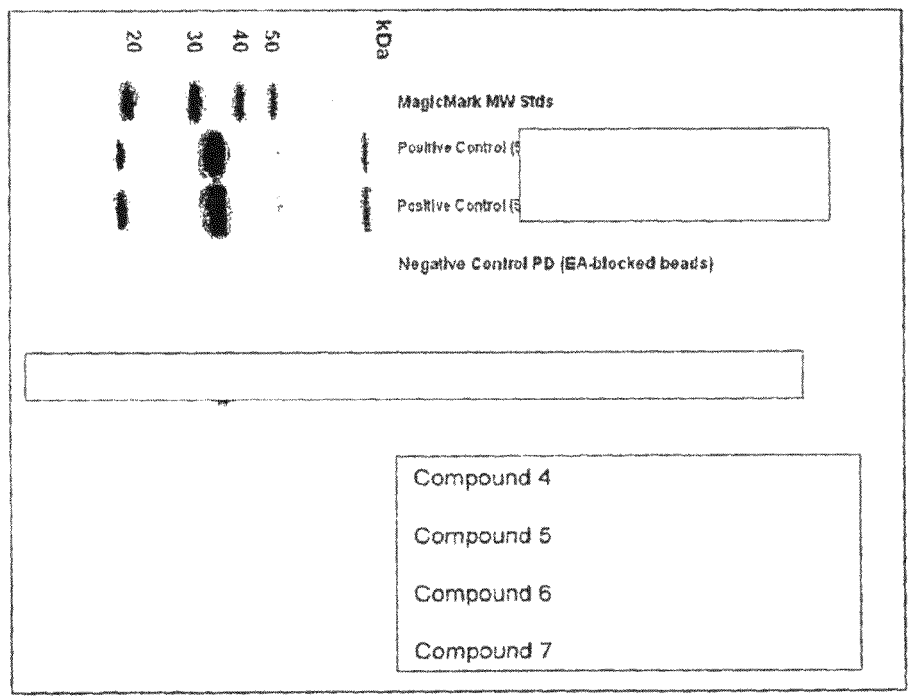
FIG. 4 shows proteins identified by Western blot and SDS-PAGE from pull-down experiments using lysates from tumor cells with Compounds 4-9 immobilized on Affi-Gel 10 beads.
Figure 4:
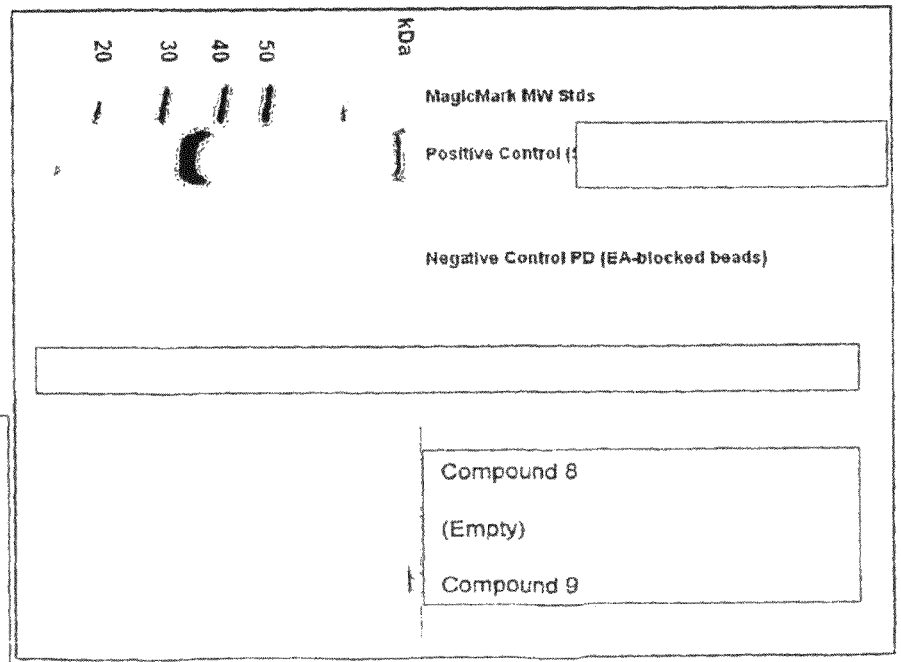

Compounds 2 and 3, shown in FIGS. 3 and 4, inhibited proliferation of HT-1080 cells with IC50 values of 100 nM and 200 nM respectively.

Example 4

Inhibition of Growth of HT-1080 Cells

The ability of various compounds of the invention, in DMSO, to inhibit the growth of HT-1080 cells was measured. The HT-1080 cell line used in these experiments was derived from a patient with fibrosarcoma and harbors an activating mutation in the N-ras gene at codon 12. The compound was assayed using the assay described in Example 3. The results of the assay are shown in the table below, where the activity corresponds to the following ranges: A—less than 10 nM, B—10-100 nM, C—100-1000 nM, D—1000-2000 nM, E—greater than 2000 nM.

| Structure | Name | Compound # | Activity |
|---|---|---|---|
| 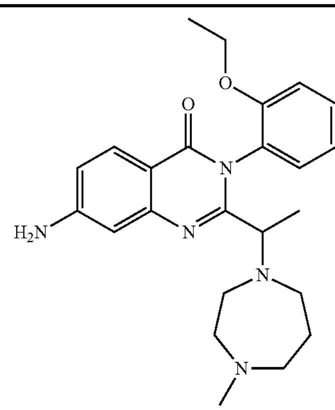 | 7-amino-3-(2-ethoxyphenyl)-2-(1-(4-methyl-1,4-diazepan-1-yl)ethyl)quinazolin-4(3H)-one | 10 | A |

-continued

| Structure | Name | Compound # | Activity |
|---|---|---|---|
| 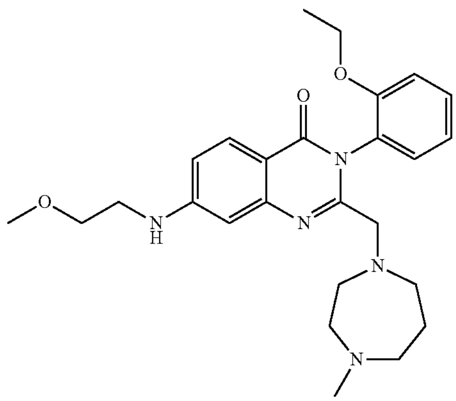 [SMILES: CCOc1ccccc1-n1c(CN2CCCN(C)CC2)nc2cc(NCCOC)ccc2c1=O] | 3-(2-ethoxyphenyl)-7-(2-methoxyethylamino)-2-((4-methyl-1,4-diazepan-1-yl)methyl)quinazolin-4(3H)-one | 11 | E |
| 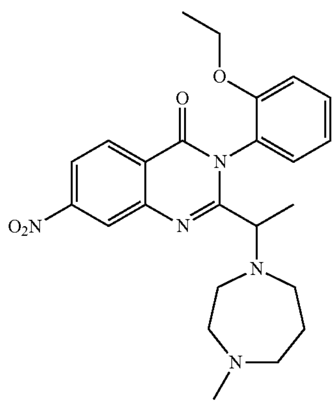 [SMILES: CCOc1ccccc1-n1c(C(C)N2CCCN(C)CC2)nc2cc([N+](=O)[O-])ccc2c1=O] | 3-(2-ethoxyphenyl)-2-(1-(4-methyl-1,4-diazepan-1-yl)ethyl)-7-nitroquinazolin-4(3H)-one | 12 | C |
| 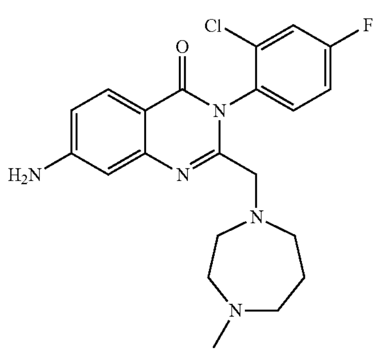 [SMILES: CN1CCCN(Cc2nc3cc(N)ccc3c(=O)n2-c2ccc(F)cc2Cl)CC1] | 7-amino-3-(2-chloro-4-fluorophenyl)-2-((4-methyl-1,4-diazepan-1-yl)methyl)quinazolin-4(3H)-one | 13 | E |
| 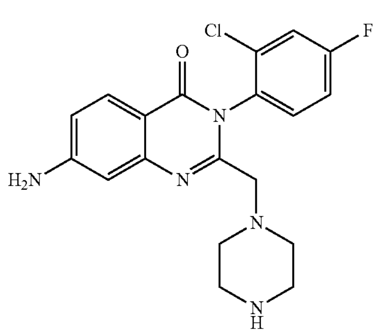 [SMILES: Nc1ccc2c(=O)n(-c3ccc(F)cc3Cl)c(CN3CCNCC3)nc2c1] | 7-amino-3-(2-chloro-4-fluorophenyl)-2-(piperazin-1-yl methyl)quinazolin-4(3H)-one | 14 | E |

-continued

| Structure | Name | Compound # | Activity |
|---|---|---|---|
| 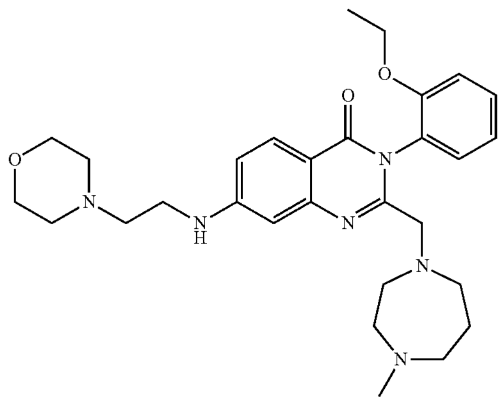 [SMILES: CCOc1ccccc1-n1c(CN2CCCN(C)CC2)nc2cc(NCCN3CCOCC3)ccc2c1=O] | 3-(2-ethoxyphenyl)-2-((4-methyl-1,4-diazepan-1-yl)methyl)-7-(2-morpholinoethylamino)quinazolin-4(3H)-one | 15 | C |
| 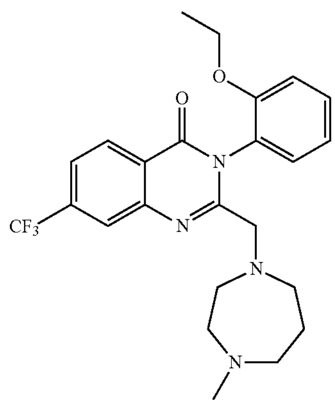 [SMILES: CCOc1ccccc1-n1c(CN2CCCN(C)CC2)nc2cc(C(F)(F)F)ccc2c1=O] | 3-(2-ethoxyphenyl)-2-((4-methyl-1,4-diazepan-1-yl)methyl)-7-(trifluoromethyl)quinazolin-4(3H)-one | 16 | C |
| 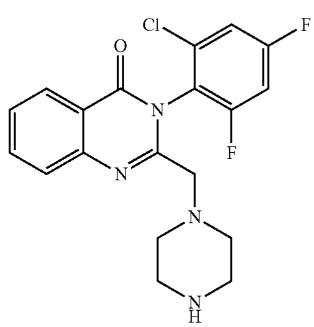 [SMILES: O=c1c2ccccc2nc(CN2CCNCC2)n1-c1c(F)cc(F)cc1Cl] | 3-(2-chloro-4,6-difluorophenyl)-2-(piperazin-1-ylmethyl)quinazolin-4(3H)one | 17 | C |
| 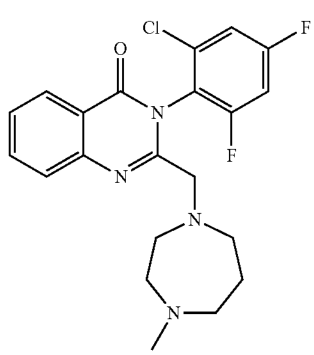 [SMILES: CN1CCCN(Cc2nc3ccccc3c(=O)n2-c2c(F)cc(F)cc2Cl)CC1] | 3-(2-chloro-4,6-difluorophenyl)-2-((4-methyl-1,4-diazepan-1-yl)methyl)quinazolin-4(3H)-one | 18 | C |

-continued

| Structure | Name | Compound # | Activity |
|---|---|---|---|
| 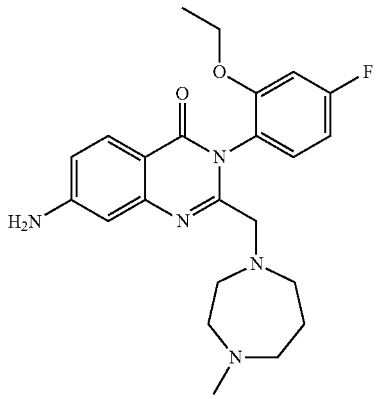 [SMILES: CCOc1cc(F)ccc1-n1c(CN2CCCN(C)CC2)nc2cc(N)ccc2c1=O] | 7-amino-3-(2-ethoxy-4-fluorophenyl)-2-((4-methyl-1,4-diazepan-1-yl)methyl)quinazolin-4(3H)-one | 19 | A |
| 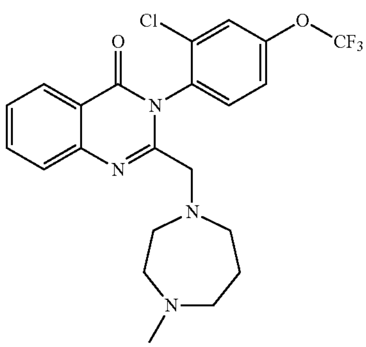 [SMILES: CN1CCCN(Cc2nc3ccccc3c(=O)n2-c2ccc(OC(F)(F)F)cc2Cl)CC1] | 3-(2-chloro-4-(trifluoromethoxy)phenyl)-2-((4-methyl-1,4-diazepan-1-yl)methyl)quinazolin-4(3H)-one | 20 | B |
| 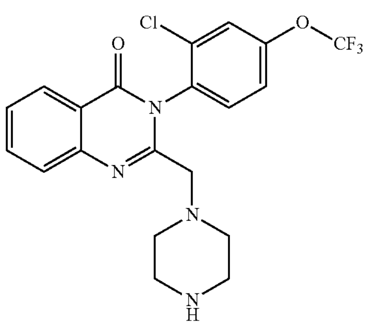 [SMILES: O=c1c2ccccc2nc(CN2CCNCC2)n1-c1ccc(OC(F)(F)F)cc1Cl] | 3-(2-chloro-4-(trifluoromethoxy)phenyl)-2-(piperazin-1-ylmethyl)quinazolin-4(3H)-one | 21 | C |
| 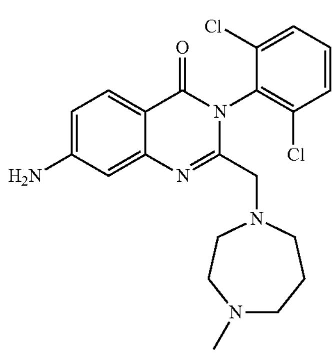 [SMILES: CN1CCCN(Cc2nc3cc(N)ccc3c(=O)n2-c2c(Cl)cccc2Cl)CC1] | 7-amino-3-(2,6-dichlorophenyl)-2-((4-methyl-1,4-diazepan-1-yl)methyl)quinazolin-4(3H)-one | 22 | C |

| Structure | Name | Compound # | Activity |
|---|---|---|---|
| 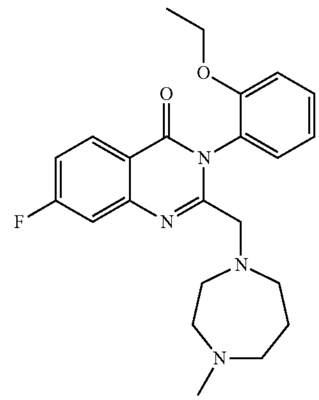 [SMILES: CCOc1ccccc1-n1c(CN2CCCN(C)CC2)nc2cc(F)ccc2c1=O] | 3-(2-ethoxyphenyl)-7-fluoro-2-((4-methyl-1,4-diazepan-1-yl)methyl)quinazolin-4(3H)-one | 24 | C |
| 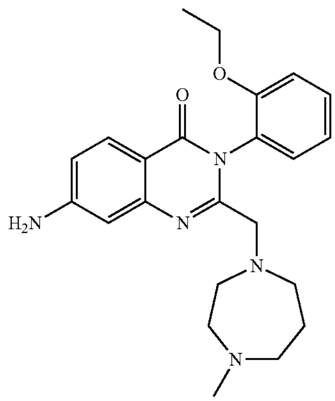 | 7-amino-3-(2-ethoxyphenyl)-2-((4-methyl-1,4-diazepan-1-yl)methyl)quinazolin-4(3H)-one | 25 | A |
| 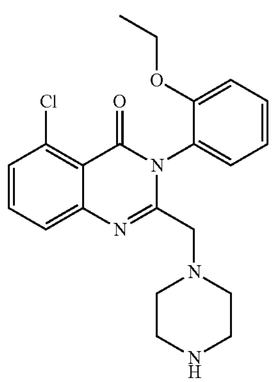 [SMILES: CCOc1ccccc1-n1c(CN2CCNCC2)nc2cccc(Cl)c2c1=O] | 5-chloro-3-(2-ethoxyphenyl)-2-(piperazin-1-ylmethyl)quinazolin-4(3H)-one | 2 | B |
| 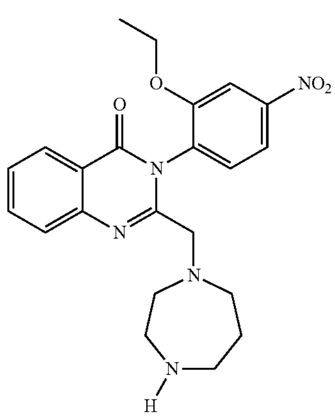 [SMILES: CCOc1cc([N+](=O)[O-])ccc1-n1c(CN2CCCNCC2)nc2ccccc2c1=O] | 2-((1,4-diazepan-1-yl)methyl)-3-(2-ethoxy-4-nitrophenyl)quinazolin-4(3H)-one | 3 | C |

Example 5

Treatment of Tumor Xenografts

The ability of compounds 10 and 25 to inhibit the growth of HT-1080 xenografts following daily, intravenous administration was examined using similar methods (described below). Compounds 10 and 25 were administered for 5 consecutive days and were evaluated at their respective IV MTD doses.

Summary:

The HT-1080 cell line used in this xenograft study was derived from a patient with fibrosarcoma and harbors an activating mutation in the N-ras gene at codon 12. The compounds inhibited HT-1080 tumor growth. Robust tumor regression was observed when the compounds were administered at their respective MTD. No adverse clinical signs were observed Mouse Strain:

Nude Balb/c (Nu/Nu strain, Charles River Laboratories), female, 5-6 wks. old (~22 g average body weight).

Study Groups:

A: Untreated Control, n=6
B: Vehicle Control for Compound 10, QD×5 days, IV, n=6
D: Compound 10 @ 25 mg/Kg (MTD), QD×5 days, IV, n=6
E: Compound 10 @ 12.5 mg/Kg (½ MTD), QD×5 days, IV, n=6

Treatment Schedule:

Beginning when the mean tumor volume reached ~300 mm$^3$ and the tumors began to actively grow (study day 1), and continuing through day 5, every day, each animal was administered a single IV injection of one of the above treatments, for a total of 5 treatments Tumor Implants and Staging:

Each of 50 mice was implanted with 1×10$^7$ HT-1080 cells by SC injection of 0.1 cc of inoculum into the right hind flank. A 26 G×⅜" needle size was used The tumor cell inoculum was prepared using HT-1080 cells (ATCC isolate, 6$^{th}$ passage freezer stock) which had been cultured in DMEM [Gibco, No. 10569-010]+10% FCS [Gibco, No. F-2442]. At the time of cell harvest, cells had grown to 95-100% confluence. HT-1080 inoculum was prepared in sterile DMEM medium+10% FCS at a density of 1.0×10$^8$ cells/ml. On day +10 post-tumor implant, the animals were group-matched into treatment and control groups, with each group consisting of 6 mice. A total of 14 outliers were excluded from the study due to tumors that were either too small or too large. This was considered study Day 1, and treatment was initiated on this day.

Preparation of Compound 10 Stock Solution:

On the morning of each day of compound administration, a Compound 10 stock solution was prepared fresh, to a concentration of 20 mg/ml by first dissolving 20 mg of Compound 10 to a final volume of 0.2 ml, in a solvent consisting of 400 mM HCl in water. The resulting 100 mg/ml solution was then diluted 1:5 to a concentration of 20 mg/ml using a diluent which consisted of 1.1% (78 mM) dibasic sodium phosphate and 3% (90 mM) sucrose. This was done by mixing the 0.2 ml volume of 100 mg/ml solution with 0.8 ml of diluent. The resulting solution was pH=6.8 and 304 mOsm. This solution was then filter-sterilized (0.45 μm), and was used for the preparation of final injection solutions (see below).

Preparation of Compound 10 Injection Solutions:

On each of the 5 days on which the compound was administered, injection solutions were prepared by dilution of the 20 mg/ml stock solution using 5% Dextrose for injection (Baxter, No. 2B0064, NDC 0338-0017-04), as shown in the table below (Concentrations of the 2 injection solutions were based on an average body weight of 22.0 gms):

| Study Group | Dose mg/Kg | Conc'n of Injection Sol'n | Dilution factor from 20 mg/ml | Prep'n of Injection Solution ml of stock | ml diluent |
|---|---|---|---|---|---|
| D | 25 | 2.75 mg/ml | 7.27 | 0.275 | 1.725 |
| E | 12.5 | 1.375 mg/ml | 14.54 | 0.138 | 1.862 |

Vehicle Control for Compound 10:

A vehicle control was prepared by first mixing 0.1 ml of 400 mM HCl with 0.4 ml of diluent which consisted of 1.1% (78 mM) dibasic sodium phosphate and 3% (90 mM) sucrose. The resulting solution was then further diluted, 1:7.27, by the addition of 3.135 ml of 5% Dextrose for injection (Baxter, No. 2B0064, NDC 0338-0017-04). The pH of the solution was then adjusted to 7.4 using 5M NaOH. The final solution corresponded to the vehicle present in the injection solution prepared for group D, but without the compound present. The vehicle control solution was filter-sterilized prior to administration.

Dosing Summary (Based on a Mean Body Weight=22.0 gms.):

| Study Group | Treatment | Conc'n of Inj. Sol'n | Amt. Compound Given (mg) | Volume of Inj. Sol'n Given |
|---|---|---|---|---|
| B | Vehicle Control, Compound 10 | 0 mg/ml | Vehicle Only | 0.2 ml |
| D | Compound 10 @ 25 mg/Kg | 2.75 mg/ml | 0.55 | 0.2 ml |
| E | Compound 10 @ 12.5 mg/Kg | 1.375 | 0.275 | 0.2 ml |

Tumor Measurement:

Starting on Day 1, all animals were weighed, and tumor dimensions (L & W) were measured, every other day. The tumor measurements were then converted to tumor volume (mm$^3$) using the following formula:

$$\text{Tumor Volume} = L \times W \times W/2$$

The resulting tumor volume values were averaged for each study group for each time point, and were then plotted against time. Variance was expressed as standard error of the mean (±SEM). The results of these experiments are shown in FIGS. 1-3.

Xenograft studies indicate that the chosen compounds are capable of causing robust HT-1080 tumor regression. No adverse clinical symptoms were observed in the animals that were dosed with the Prolexys compounds. These compounds therefore exhibit tumor-selective cell death.

Example 6

Identification of Compounds with Increased Potency or Activity in the Presence of Specific Cancer-Related Alleles Described here is a method to identify compounds with increased potency or activity in the presence of RAS$^{V12}$. Although the method described herein uses RAS$^{V12}$ as a transforming gene, other studies can make use of a wide variety of cancer-associated alleles using this methodology in order to define the signaling networks that involve many oncogenes and tumor suppressors. The primary screen tests the effect of treating tumorigenic cells with each compound for 48 hours at a concentration of 4 µg/mL, corresponding to 10 µM for a compound with a molecular weight of 400. Cell viability is measured using the Sytox method described above or the dye calcein acetoxymethyl ester (calcein AM) (Wang et al., 1993, Hum. Immunol. 37, 264-270), which is a non-fluorescent compound that freely diffuses into cells. In live cells, calcein AM is cleaved by intracellular esterases, forming the anionic fluorescent derivative calcein, which cannot diffuse out of live cells. Hence, live cells exhibit a green fluorescence when incubated with calcein AM, whereas dead cells do not, dead and dying cells fluoresce when incubated with Sytox. Compounds that induce fluorescence that is distinguishable from that observed in the control cells are subsequently tested in a dilution series in control and tumorigenic cells to identify compounds that display synthetic lethality, which is lethality in tumorigenic cells but not in isogenic primary cells.

Example 7

Identification and Characterization of Binding Partners of Compounds

Pull-down assays using immobilized compounds of the invention and cell lysates are used to identify binding partners for compounds of the invention inside a cell. Pull-down experiments are performed with whole tumor cell lysates. In these experiments, a compound of the invention is immobilized to Affigel 10 and incubated with lysate under standard pull-down conditions. The beads are washed and either eluted with 100 µM erastin or a compound of the invention or 0.8% N-lauroylsarcosine (sarkosyl). The eluates are subjected to mass spectrometric analysis.

FIG. 4 shows the results of a pull-down assay using BJELR whole cell lysates and Compounds (4)-(9).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound represented by Structural Formula (I):

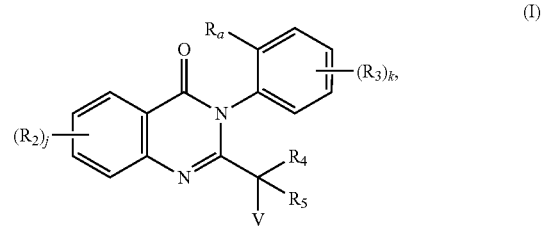

or a pharmaceutically acceptable salt thereof, wherein
$R_a$ is a halogen, substituted or unsubstituted alkyl, substituted or unsubstituted alkenyl, substituted or unsubstituted alkynyl, substituted or unsubstituted aryl-O—, substituted or unsubstituted alkyl-O—, substituted or unsubstituted alkenyl-O— or substituted or unsubstituted alkynyl-O—, wherein alkyl, alkenyl and alkynyl are optionally interrupted by NR, O or S(O)$_n$;
each $R_2$ is independently selected from the group consisting of substituted or unsubstituted alkyl, substituted or unsubstituted aryl, substituted or unsubstituted non-aromatic heterocyclic, —CN, —COOR', —CON(R)$_2$, —NRC(O)R, —SO$_2$N(R)$_2$, —N(R)$_2$, —OH and —OR';
each $R_3$ is independently selected from the group consisting of halogen, substituted or unsubstituted alkyl, substituted or unsubstituted aryl, substituted or unsubstituted non-aromatic heterocyclic, —CN, —COOR', —CON(R)$_2$, —NRC(O)R, ⁻SO$_2$N(R)$_2$, —N(R)$_2$, —NO$_2$, —OH and —OR';
$R_4$ and $R_5$ are independently selected from the group consisting of —H, substituted or unsubstituted alkyl, substituted or unsubstituted alkenyl, substituted or unsubstituted alkynyl, substituted or unsubstituted non-aromatic heterocyclic and substituted or unsubstituted aryl, wherein alkyl, alkenyl and alkynyl are optionally interrupted by NR, O or S(O)$_n$; or $R_4$ and $R_5$ taken together form a carbocyclic or heterocyclic group;
V is —NH-L-A-Q or

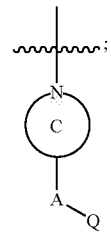

Ring C is a substituted or unsubstituted heterocyclic aromatic or non-aromatic ring; A is NR or O; or A is a covalent bond;
L is a substituted or unsubstituted hydrocarbyl group optionally interrupted by one or more heteroatoms selected from N, O and S;
Q is selected from the group consisting of —R, —C(O)R', —C(O)N(R)$_2$, —C(O)OR' and —S(O)$_2$R';
each R is independently —H, substituted or unsubstituted alkyl, substituted or unsubstituted alkenyl, substituted or unsubstituted alkynyl, substituted or unsubstituted aryl or substituted or unsubstituted non-aromatic heterocyclic;

each R' is independently a substituted or unsubstituted alkyl, substituted or unsubstituted alkenyl, substituted or unsubstituted alkynyl group, substituted or unsubstituted non-aromatic heterocyclic or substituted or unsubstituted aryl group;

j is an integer from 1 to 4;

k is an integer from 0 to 4; and each n is independently 0, 1 or 2.

2. The compound of claim 1, wherein V is

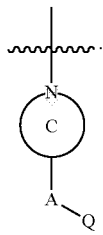

3. The compound of claim 2, wherein V is

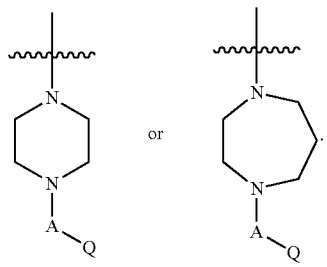

4. The compound of claim 3, wherein Q is —C(O)R' or —R.

5. The compound of claim 4, wherein Q is —H, methyl or ethyl.

6. The compound of claim 2, wherein A is a covalent bond or NR.

7. The compound of claim 2, wherein $R_4$ and $R_5$ are —H or a substituted or unsubstituted alkyl group.

8. The compound of claim 7, wherein $R_4$ and $R_5$ are —H or an unsubstituted C1-C4 alkyl group.

9. The compound of claim 2, wherein $R_a$ is a substituted or unsubstituted alkyl-O— group.

10. The compound of claim 9, wherein $R_a$ is an unsubstituted alkyl-O— group.

11. The compound of claim 1, wherein $R_2$ is independently selected from the group consisting of —NRC(O)R, —NR$_2$, halogen, polar substituted alkyl, polar substituted carbocyclic aryl, substituted or unsubstituted heteroaryl and substituted or unsubstituted non-aromatic heterocyclic.

12. The compound of claim 1, wherein the compound is represented by Structural Formula (Ia):

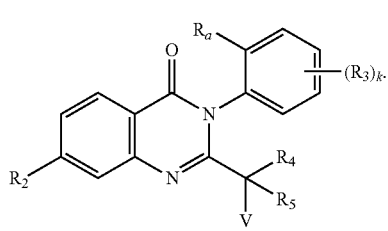

13. The compound of claim 1, wherein k is an integer from 1 to 4.

14. The compound of claim 13, wherein each $R_3$ is independently selected from the group consisting of polar substituted alkyl, polar substituted carbocyclic aryl, substituted or unsubstituted heteroaryl and substituted or unsubstituted non-aromatic heterocyclic.

15. The compound of claim 13, wherein the compound is represented by Structural Formula (Ib):

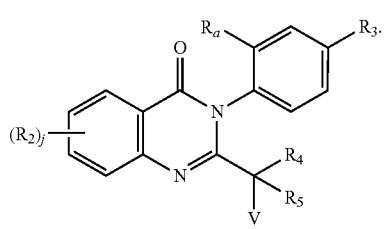

16. A compound represented by Structural Formula (II):

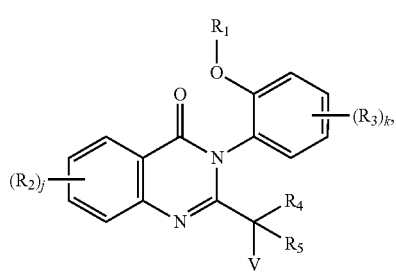

or a pharmaceutically acceptable salt thereof, wherein:
  $R_1$ is a substituted or unsubstituted alkyl, substituted or unsubstituted alkenyl or substituted or unsubstituted alkynyl group, each of which is optionally interrupted by NR, O or $S(O)_n$;
  each $R_2$ is independently selected from the group consisting of substituted or unsubstituted alkyl, substituted or unsubstituted aryl, substituted or unsubstituted non-aromatic heterocyclic, —CN, $^-$CON(R)$_2$, $^-$SO$_2$N(R)$_2$, $^-$OH and —OR;
  each $R_3$ is independently selected from the group consisting of halogen, substituted or unsubstituted alkyl, substituted or unsubstituted aryl, substituted or unsubstituted non-aromatic heterocyclic, —CN, —COOR', —CON(R)$_2$, —SO$_2$N(R)$_2$, —OH and —OR';

R$_4$ and R$_5$ are independently selected from the group consisting of —H, substituted or unsubstituted alkyl, substituted or unsubstituted alkenyl, substituted or unsubstituted alkynyl, substituted or unsubstituted non-aromatic heterocyclic and substituted or unsubstituted aryl, wherein alkyl, alkenyl and alkynyl are optionally interrupted by NR, O or S(O)$_n$; or R$_4$ and R$_5$ taken together form a carbocyclic or heterocyclic group;

V is —NH-L-A-Q or

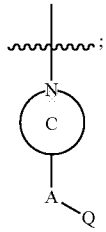

Ring C is a substituted or unsubstituted heterocyclic aromatic or non-aromatic ring; A is NR or O; or A is a covalent bond;

L is a substituted or unsubstituted hydrocarbyl group optionally interrupted by one or more heteroatoms selected from N, O and S;

Q is selected from the group consisting of —R, —C(O)R', —C(O)N(R)$_2$, —C(O)OR' and —S(O)$_2$R';

each R is independently —H, substituted or unsubstituted alkyl, substituted or unsubstituted alkenyl, substituted or unsubstituted alkynyl, substituted or unsubstituted aryl or substituted or unsubstituted non-aromatic heterocyclic;

each R' is independently a substituted or unsubstituted alkyl, substituted or unsubstituted alkenyl, substituted or unsubstituted alkynyl group, substituted or unsubstituted non-aromatic heterocyclic or substituted or unsubstituted aryl group;

j is an integer from 1 to 4;
k is an integer from 0 to 4; and
each n is independently 0, 1 or 2.

17. A pharmaceutical composition comprising a compound of any of claims 1 and 16 and a pharmaceutically acceptable carrier.

18. The compound of claim 12, wherein V is

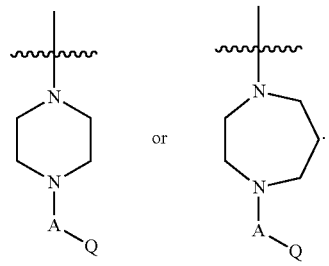

19. The compound of claim 18, wherein A is a covalent bond and Q is —H, methyl or ethyl.

20. The compound of claim 18, wherein R$_4$ and R$_5$ are —H or an unsubstituted C1-C4 alkyl group.

21. The compound of claim 18, wherein R$_a$ is an unsubstituted alkyl-O— group.

22. The compound of claim 18, wherein R$_2$ is —NHR.

23. The compound of claim 18, wherein R$_2$ is —NH$_2$.

24. The compound of claim 23, wherein A is a covalent bond and Q is —H, methyl or ethyl.

25. The compound of claim 23, wherein R$_4$ and R$_5$ are —H or an unsubstituted C1-C4 alkyl group.

26. The compound of claim 23, wherein R$_a$ is ethoxy.

27. A compound that is

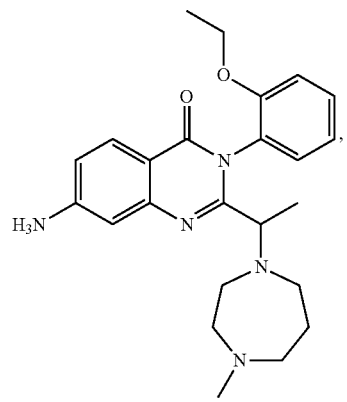

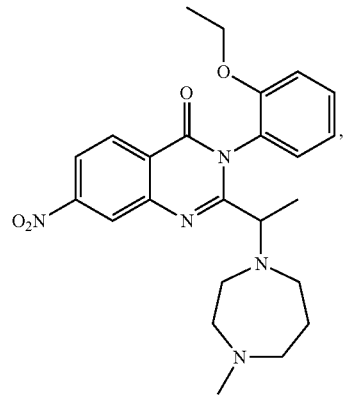

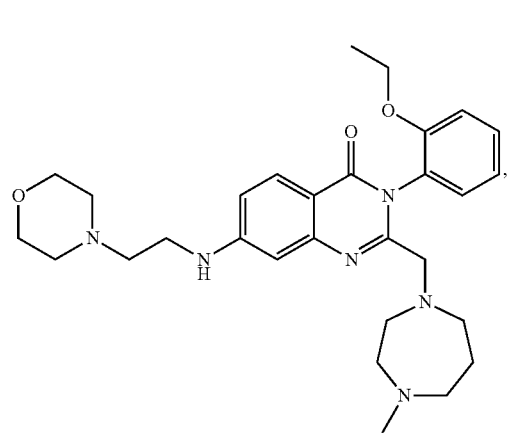

-continued
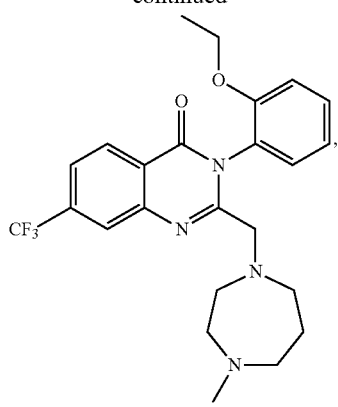
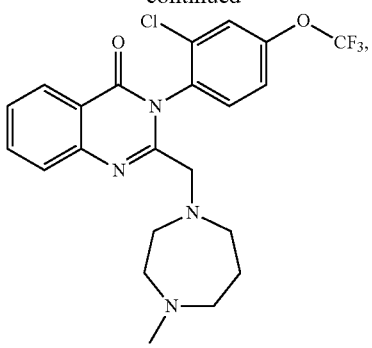
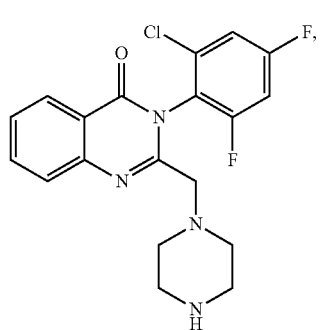
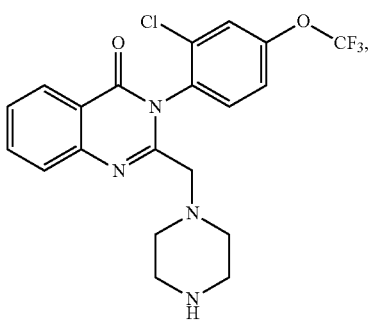
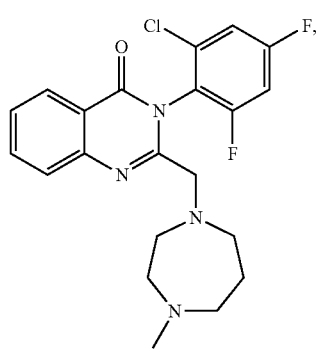
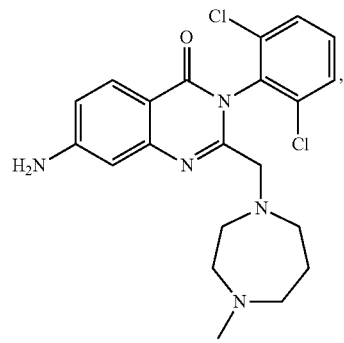
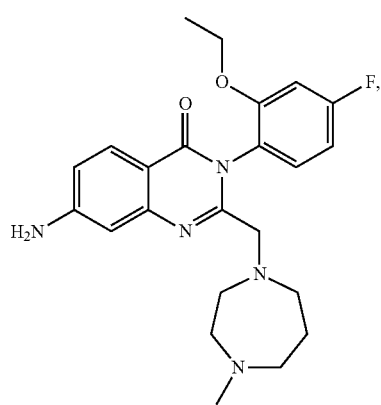
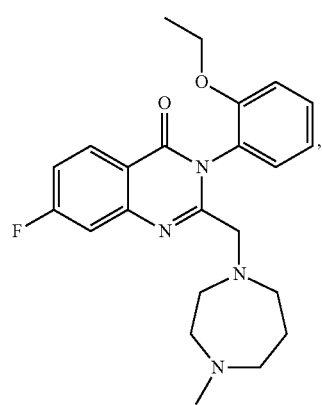

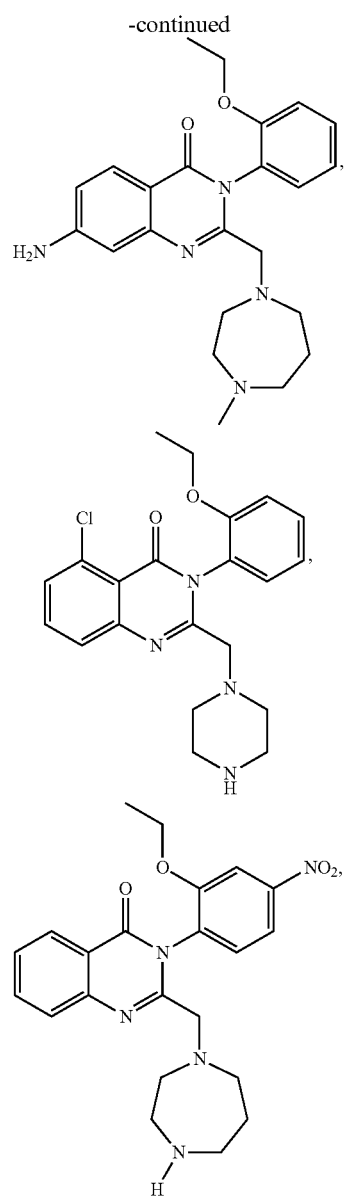
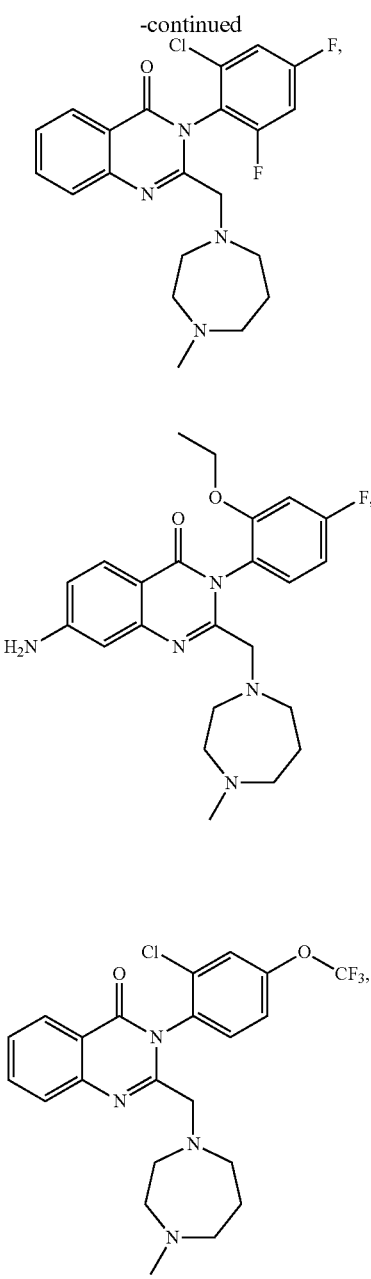
or pharmaceutically acceptable salt thereof.
28. The compound of claim 27 that is
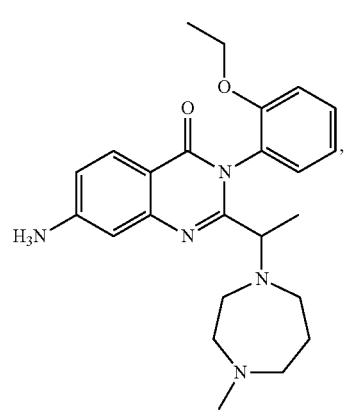
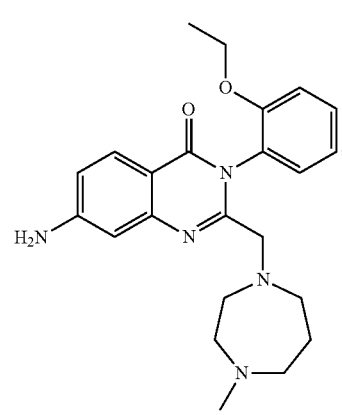

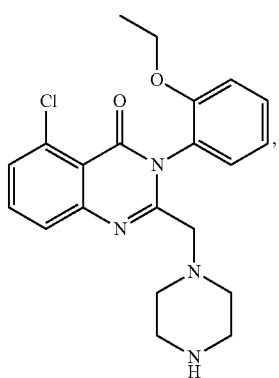
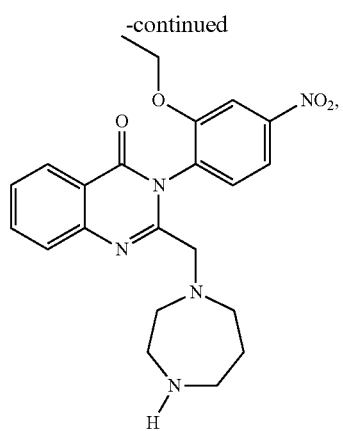
or pharmaceutically acceptable salt thereof.
* * * * *